US010342897B2

(12) United States Patent
Altschuler

(10) Patent No.: US 10,342,897 B2
(45) Date of Patent: Jul. 9, 2019

(54) BIOMATRIX HYDROGELS AND METHODS OF USE THEREOF

(71) Applicant: CARTIHEAL (2009) LTD, Kfar Saba (IL)

(72) Inventor: Nir Altschuler, Zur Yitschak (IL)

(73) Assignee: Cartiheal (2009) Ltd, Kfar Saba (IL)

( * ) Notice: Subject to any disclaimer, the term of this patent is extended or adjusted under 35 U.S.C. 154(b) by 0 days.

(21) Appl. No.: 14/401,555

(22) PCT Filed: Apr. 29, 2013

(86) PCT No.: PCT/IL2013/050364
§ 371 (c)(1),
(2) Date: Nov. 17, 2014

(87) PCT Pub. No.: WO2013/171736
PCT Pub. Date: Nov. 21, 2013

(65) Prior Publication Data
US 2015/0147397 A1    May 28, 2015

Related U.S. Application Data

(60) Provisional application No. 61/773,228, filed on Mar. 6, 2013, provisional application No. 61/773,219, filed on Mar. 6, 2013, provisional application No. 61/764,467, filed on Feb. 13, 2013, provisional application No. 61/764,496, filed on Feb. 13, 2013, provisional application No. 61/763,985, filed on Feb. 13, 2013, provisional application No. 61/763,981, filed on Feb. 13, 2013, provisional application No. 61/648,089, filed on May 17, 2012, provisional application No. 61/648,087, filed on May 17, 2012.

(51) Int. Cl.
| A61F 2/28 | (2006.01) |
| A61L 24/00 | (2006.01) |
| A61L 27/36 | (2006.01) |
| A61L 27/38 | (2006.01) |
| A61L 27/44 | (2006.01) |
| A61L 27/46 | (2006.01) |
| A61L 27/52 | (2006.01) |
| A61L 27/54 | (2006.01) |
| A61L 27/20 | (2006.01) |
| A61L 27/24 | (2006.01) |

(52) U.S. Cl.
CPC ........... *A61L 27/3604* (2013.01); *A61F 2/28* (2013.01); *A61L 24/0084* (2013.01); *A61L 27/20* (2013.01); *A61L 27/24* (2013.01); *A61L 27/365* (2013.01); *A61L 27/3654* (2013.01); *A61L 27/3834* (2013.01); *A61L 27/446* (2013.01); *A61L 27/46* (2013.01); *A61L 27/52* (2013.01); *A61L 27/54* (2013.01); *A61L 2430/02* (2013.01); *A61L 2430/06* (2013.01)

(58) Field of Classification Search
None
See application file for complete search history.

(56) References Cited

U.S. PATENT DOCUMENTS

| 6,506,217 | B1 * | 1/2003 | Arnett ............... A61L 27/12 128/898 |
| 8,790,681 | B2 | 7/2014 | Altschuler et al. |
| 8,802,115 | B2 | 8/2014 | Altschuler et al. |
| 8,808,725 | B2 | 8/2014 | Altschuler et al. |
| 8,932,581 | B2 | 1/2015 | Vago |
| 9,770,531 | B2 | 9/2017 | Altschuler |
| 2002/0128618 | A1 * | 9/2002 | Frenz ............... A61L 15/60 604/368 |
| 2003/0143283 | A1 * | 7/2003 | Tofe ............... A61K 35/32 424/549 |
| 2006/0198863 | A1 * | 9/2006 | DePaula ........... A61K 31/728 424/422 |
| 2009/0028954 | A1 * | 1/2009 | Bohner ............... A61L 27/46 424/489 |
| 2011/0200563 | A1 * | 8/2011 | Vago ............... A61K 35/614 424/93.7 |
| 2014/0287017 | A1 | 9/2014 | Altschuler et al. |
| 2015/0056262 | A1 | 2/2015 | Altschuler et al. |
| 2015/0134065 | A1 | 5/2015 | Altschuler |
| 2015/0289889 | A1 | 10/2015 | Altschuler et al. |
| 2015/0359931 | A1 | 12/2015 | Vago |
| 2016/0000969 | A1 | 1/2016 | Altschuler |
| 2016/0175098 | A1 | 6/2016 | Altschuler |
| 2016/0175480 | A1 | 6/2016 | Altschuler et al. |
| 2016/0184477 | A1 | 6/2016 | Altschuler |

FOREIGN PATENT DOCUMENTS

| WO | WO 2009/066283 A2 | 5/2009 |
| WO | WO 2010/058400 A1 | 5/2010 |
| WO | WO 2010/146575 A2 | 12/2010 |
| WO | WO 2016/178226 A1 | 11/2016 |

OTHER PUBLICATIONS

Ni et al. Biomaterials 2003 24:4323-4331 (Year: 2003).*
Reinares-Fisac et al. ChrystEngComm 2017 19:110-116 (Year: 2017).*
Deb et al. Biomaterials 1995 16(14): 1095-1100 (Year: 1995).*
International Search Report (ISR) for PCT/I12013/050364; I.A. fd Apr. 29, 2013, dated Jul. 26, 2013 from the European Patent Office, Rijswijk, Netherlands.
International Preliminary Report on Patentability (Chapter I of the Patent Cooperation Treaty) including the Written Opinion of the International Searching Authority for PCT/IL2013/050364; I.A. fd Apr. 29, 2013, dated Nov. 18, 2014, from the International Bureau of WIPO, Genera, Switzerland.

(Continued)

Primary Examiner — Robert A Wax
Assistant Examiner — Caralynne E Helm
(74) Attorney, Agent, or Firm — Sterne, Kessler, Goldstein & Fox P.L.L.C.

(57) ABSTRACT

This invention is directed to aragonite and calcite hydrogel biomatrices, optionally seeded with precursor cells and uses thereof in tissue engineering, regeneration and repair, including in inducing or enhancing bone formation, cartilage formation or a combination thereof in a subject, and kits related thereto.

38 Claims, 8 Drawing Sheets

(56) References Cited

OTHER PUBLICATIONS

Xu, Y et al., "Hydrothermal conversion of coral into hydroxyapatite," Materials Characterization, Aug. 2001, 47(2): 83-87, Elsevier B.V, Netherlands.
Communication pursuant to Article 94(3) EPC, for EP application No. 13 728 251.3, dated Jan. 29, 2018, European Patent Office, Rijswijk, Netherlands.
Excerpted file history, U.S. Appl. No. 14/767,428: Final rejection (dated Feb. 21, 2018); Amendment and reply (dated Nov. 8, 2017); Non-final rejection (dated May 11, 2017) and Preliminary amendment (dated Nov. 10, 2015).

* cited by examiner

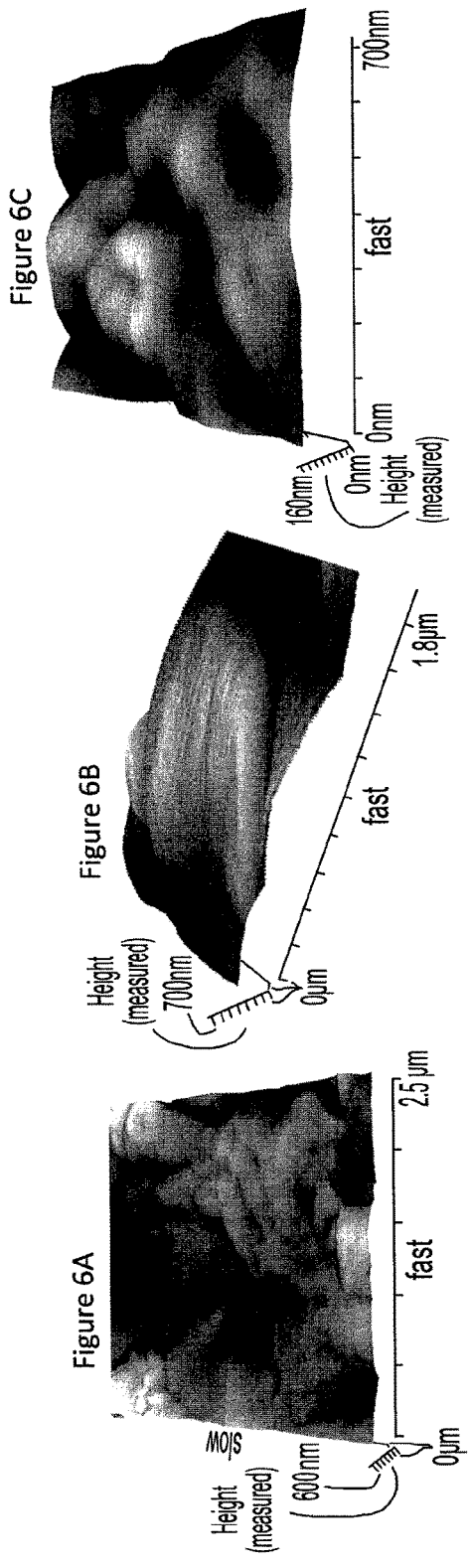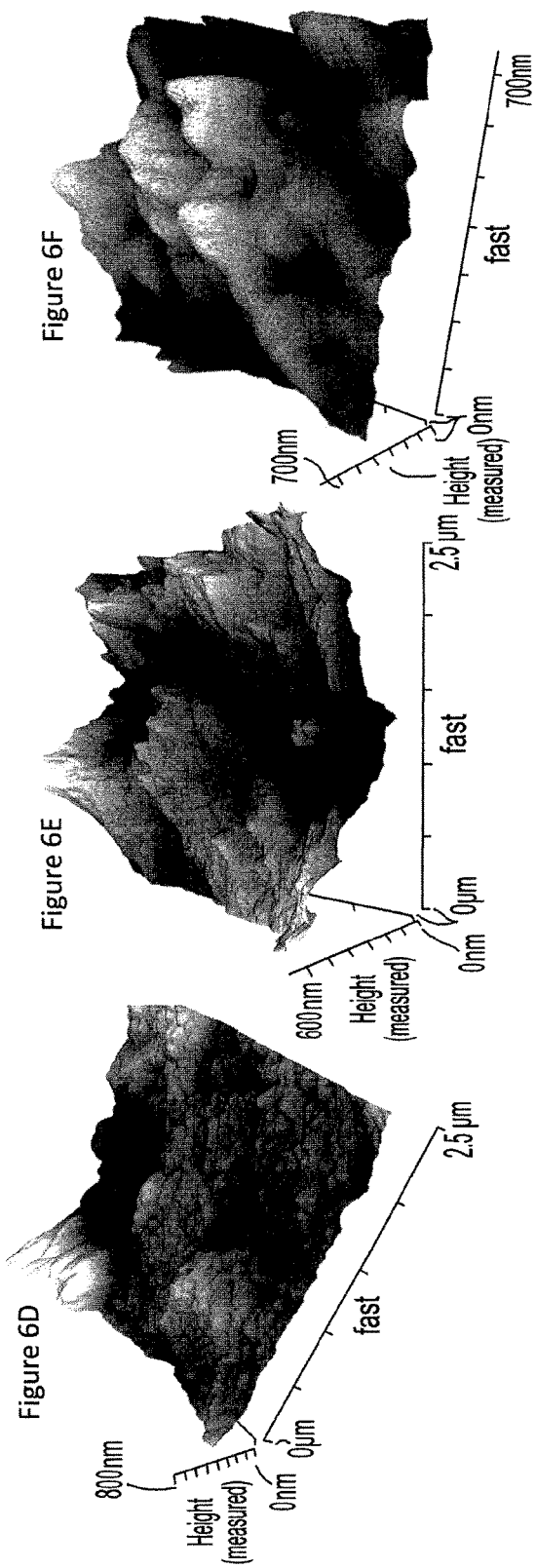

BIOMATRIX HYDROGELS AND METHODS OF USE THEREOF

CROSS REFERENCE TO RELATED APPLICATIONS

This application claims the benefit of U.S. Provisional Application Ser. No. 61/648,089 filed May 17, 2012, U.S. Provisional Application Ser. No. 61/648,087 filed May 17, 2012, U.S. Provisional Application Ser. No. 61/763,981 filed Feb. 13, 2013, U.S. Provisional Application Ser. No. 61/763, 985 filed Feb. 13, 2013, U.S. Provisional Application Ser. No. 61/764,467 filed Feb. 13, 2013, U.S. Provisional Application Ser. No. 61/764,496 filed Feb. 13, 2013, U.S. Provisional Application Ser. No. 61/773,219 filed Mar. 6, 2013 U.S. Provisional Application Ser. No. 61/773,228 filed Mar. 6, 2013, all of which are hereby incorporated by reference herein in their entirety.

BACKGROUND OF THE INVENTION

Surgical intervention and grafting are sometimes necessary to restore mechanical function and reconstruct the morphology of bone and cartilage, resulting from trauma, tumors, or abnormal bone developments.

Synthetic materials such as metals, calcium salts and bone cements have also been used for restoring and reconstructing bone for many years, but often result in stress-shielding to the surrounding bone and fatigue failure of the implant. Another possibility is autologous bone grafting, although the supply of autologous bone tissue is limited and bone harvesting is painful, with the risk of infection, hemorrhage, aesthetic damage, nerve damage, and loss of bone function. In addition, significant morbidity is associated with autograft harvest sites. These problems may be overcome by tissue engineering of scaffolds made of synthetic or natural biomaterials that promote the adhesion, migration, proliferation, and differentiation of bone marrow stem cells, also known as mesenchymal stem cells (MSCs). An association between biocomponents and biologic regenerative and repair responses can be promoted by providing a scaffold containing spaces morphologically compatible with osteons and their vascular interconnections.

The immediate microenvironment and the three-dimensional (3D) organization are important factors in differentiation in general and particularly in osteogenic differentiation.

Some bone tissue engineering scaffolds consists of natural polymers, such as collagen, alginate, hyaluronic acid, and chitosan. Natural materials offer the advantages of specific cell interaction, easy seeding of cells because of their hydrophilic interactions, low toxicity and low chronic inflammatory response. However, these scaffolds often are mechanically unstable and do not readily contribute to the creation of tissue structures with a specific predefined shape for transplantation. To obtain mechanical strength, chemical modification is required, which may lead to toxicity.

Defects and degeneration of the articular cartilage surfaces of joints causes pain and stiffness. Damage to cartilage which protects joints can result from either physical injury as a result of trauma, sports or repetitive stresses (e.g., osteochondral fracture, secondary damage due to cruciate ligament injury) or from disease (e.g. osteoarthritis, rheumatoid arthritis, aseptic necrosis, osteochondritis dissecans).

Osteoarthritis (OA) results from general wear and tear of joints, most notably hip and knee joints. Osteoarthritis is common in the elderly but, in fact, by age 40 most individuals have some osteoarthritic changes in their weight bearing joints. Another emerging trend increasing the prevalence of osteoarthritis is the rise in obesity. The CDC estimates that 30% of American adults (or 60 million people) are obese. Obese adults are 4 times more likely to develop knee OA than normal weight adults Rheumatoid arthritis is an inflammatory condition which results in the destruction of cartilage. It is thought to be, at least in part, an autoimmune disease with sufferers having a genetic predisposition to the disease.

Orthopedic prevention and repair of damaged joints is a significant burden on the medical profession both in terms of expense and time spent treating patients. In part, this is because cartilage does not posses the capacity for self-repair. Attempts to re-grow hyaline cartilage for repair of cartilage defects remain unsuccessful.

Orthopedic surgery is available in order to repair defects and prevent articular damage in an effort to forestall serious degenerative changes in a joint. The use of surgical techniques often requires the removal and donation of healthy tissue to replace the damaged or diseased tissue. Techniques utilizing donated tissue from autografts, allografts, or xenografts are wholly unsatisfactory as autografts add additional trauma to a subject and allografts and xenografts are limited by immunological reactivity to the host subject and possible transfer of infective agents. Surgical attempts to utilize materials other than human or animal tissue for cartilage regeneration have been unsuccessful.

The restoration of one or more teeth in a patient's mouth using artificial components is used in implant dentistry. Such artificial components typically include a dental implant and a prosthetic tooth and/or an abutment that is secured to the dental implant.

The dental implant is typically fabricated from pure titanium or a titanium alloy. The dental implant typically includes a body portion and a collar. The body portion is configured to extend into and osseointegrate with the alveolar bone. The top surface of the collar typically lies flush with the crest of the jawbone bone. The abutment (e.g., a final abutment) typically lies on the top surface and extends through the soft tissue, which lies above the alveolar bone. Recently, some dental implants have collars that extend above the crest of the jawbone and through the soft tissue.

Implants of various tapers and with various thread profiles, and comprised of different materials are known in the art.

While such prior art dental implants have been successful, there is a continuing desire to improve a dental implant's ability to osseointegrate with the alveolar bone and to improve the stability of the dental implant within the alveolar bone.

Every year several hundred thousand people require artificial hip, knee or shoulder implants (prostheses). Although such total joint prostheses have been in clinical use for decades, they are still plagued with problems of permanent, rigid fixation. Virtually all implants currently in use have a tendency to loosen with time, some to the extent of requiring revision.

There are two main techniques commonly used for fixation: cemented types using bone cement and uncemented or press-fit types. One bone cement in common use is poly(methyl methacrylate), which is applied in a dough-like state as a grouting agent between the bone and the implant. It flows around the contours of the bone and the implant and into the interstices of cancellous bone. Upon hardening, the cement forms a mechanical interlock between the bone and the implant. In effect, there is no bone in-growth linking bone and prosthesis when bone cement is used. Although bone cement gives good initial fixation, an increase in compliance often occurs due to formation of a soft tissue capsule over time. Thus, the absence of bone in-growth frequently leads to loosening of a bone-cemented prosthesis.

Press-fit prostheses are not implanted with bone cement but rather into a prepared cavity in the bone which closely approximates the prosthetic shape; long term stability of such implants requires bone to form an interlock by growing into the prosthesis at the mating surface.

Certain osteo-conductive materials (e.g., hydroxyl-apatite applied by plasma-spraying) are favored for their durability and bonding strength, but obtaining the desired press-fit at surgery is often associated with problems (Geesink, R. G. T., Clinical Orthopedics and Related Research, 261:39-58 (1990)). Further, the cavity prepared in bone to receive the prosthesis is generally not optimally shaped, causing the actual bone contact achieved with insertion of the prosthesis to be only 10-20% of the potential mating surface. The remaining voids between bone and prosthesis, containing little or no osteo-conductive material, contribute little to the bone-prosthesis interlock necessary for long-term stability of the prosthesis. There remains a need for improved prosthetic devices providing enhanced bone-prosthesis attachment stability.

Pain due to severe osteoarthritis may be associated with "intraosseous hypertension," i.e., pressure within the bone. Intra-osseous hypertension is the manifestation of edema within the bone. Thus, it has been proposed that local vascular changes may be important in the pathogenesis of degenerative arthritis and the production of its associated symptoms. It has been further observed that surgical decompression of bone (specifically in the case of osteonecrosis) can relieve bone pain. Use of surgery, however, to alleviate pressure within the bone is not ideal. For one thing, surgery can produce myriad side effects and complications, but more to the point, the problem with surgical decompression is that its benefit will be transient. The fenestrations created during so-called decompressive procedures are bound to fill with fibrocartilage. Thus, there is an ongoing need for a safe and effective method for alleviating pressure in bone causing joint pain, most typically found in patients suffering from osteoarthritis.

An ideal material which restores mechanical function and reconstructs the morphology of bone and cartilage, and/or serves as an appropriate implant material for tissue reconstructive purposes, is as yet, lacking.

SUMMARY OF THE INVENTION

In one embodiment, the present invention provides a hydrogel biomatrix comprising a marine organism skeletal derivative.

In some embodiments, this invention provides a method of tissue engineering, tissue regeneration or tissue repair in a subject comprising administering to said subject a hydrogel comprising a marine organism skeletal derivative biomatrix, wherein said marine organism skeletal derivative is characterized by a specific fluid uptake capacity value of at least 75%, which specific fluid uptake capacity value is determined by establishing a spontaneous fluid uptake value divided by a total fluid uptake value, which can participate in said tissue engineering, tissue regeneration or tissue repair In some embodiments, according to this aspect, the biomatrix is optionally seeded with a precursor cell In another embodiment, this invention provides a hydrogel biomatrix comprising a marine organism skeletal derivative biomatrix.

In another embodiment, this invention provides a hydrogel biomatrix comprising a marine organism skeletal derivative biomatrix, wherein
said marine organism skeletal derivative is characterized by a specific fluid uptake capacity value of at least 75%, which specific fluid uptake capacity value is determined by establishing a spontaneous fluid uptake value divided by a total fluid uptake value; and
said biomatrix is optionally seeded with a precursor cell, which can participate in said tissue engineering, tissue regeneration or tissue repair.

wherein said fluid is water, or a protein-containing, salt-containing or carbohydrate containing solution.

In some embodiments, the hydrogels of this invention may comprise the marine organism skeletal derivative in any appropriate weight per weight concentration, befitting the desired consistency and characteristics of use, as will be appreciated by the skilled artisan. Such hydrogels, may comprise, inter alia, biocompatible polymers, which in turn may be present in any appropriate weight per weight concentration, as well. In some embodiments, such polymer components may vary in terms of their chain length/molecular weights, or extent of cross linking. Varying these qualities, will be readily understood to the skilled artisan to serve as a means for producing a hydrogel with different characterizations such as dissolution and absorption time at implant site, strength, and tissue adhesion properties, as needed and varied to suit a particular application.

In some embodiments the hydrogel is comprised of coral or coral derivative. In some embodiments the coral or coral derivative is aragonite, calcite, hydroxyapatite, mixtures thereof, or other polymorphs of the same. In some embodiments the coral or coral derivative is isolated from a *Porites, Goniopora, Millepora* or *Acropora* species.

In some embodiments, the biomatrix comprises aragonite or calcite particles. In some embodiments, the aragonite or calcite particles have a diameter of about 1-20 microns along at least one axis of the particle. In some embodiments, the aragonite or calcite particles have a diameter of about 20-400 microns along at least one axis of the particle. In some embodiments, the aragonite or calcite particles have a diameter of about 50-800 nanometers along at least one axis of the particle. In some embodiments, the aragonite or calcite particles have a diameter of about 0.2-0.7 mm and or 0.5-0.7 mm and or 1.5-5, 4-10, 5-20 and 15-50 mm along at least one axis of the particle.

In some embodiments, the particles are spherical in shape, or in some embodiments, rod-like in shape, or in some embodiments, of any desired geometry.

In some embodiments, as will be appreciated by the skilled artisan, the invention contemplates use of very small sized particles, e.g. powders and the like, with respect to the marine organism skeletal derivative incorporated in the hydrogels as herein described. In some embodiments, as will be appreciated by the skilled artisan, the invention contemplates use of larger particles, e.g. granules and the like, with respect to the marine organism skeletal derivative incorporated in the hydrogels as herein described. According to this aspect, and in some embodiments, the larger granules may provide for enhanced vascularization and incorporation within the applied hydrogel, which in some embodiments, may correlate with access through porous structures, facilitating same.

In some embodiments, the calcite is derived from hydrothermically transformed aragonite, and in some embodiments, the hydrogels comprise native calcite. In some embodiments, the marine organism skeletal derivative may include a coral derivative that is partially or fully converted to calcite. In some embodiments, the marine organism skeletal derivative may include a coral derivative that is partially or fully converted to hydroxyapatite.

In one embodiment, the aragonite is seeded with cells, which in one embodiment are mesenchymal stem cells.

In one embodiment the hydrogel comprises chitosan, fibrinogen/thrombin, fibrin, collagen, elastin, silk, aliginate, hyaluronic acid, gelatin, guar gum, gum Arabic, xanthan, carboxymethyl cellulose, poly(vinylpyrrolidone), agar, agarose, starch, hydroxypropyl methyl cellulose, polyvinyl alcohol, poly(acrylic acid), acrylic acid, methacrylic acid, carrageenan, β-tricalcium phosphate, calcium phosphate, poly(propylene glycol), polyethylene glycol, platelet rich plasma, a glycosaminoglycan or a combination thereof. In one embodiment, the collagen comprises cross-linked collagen. In one embodiment, the glycosaminoglycan is hyaluronic acid, sodium hyaluronate, or a cross linked hyaluronic acid or a combination thereof. In one embodiment, the alginate may comprise calcium alginate, cross linked calcium alginate or a combination thereof. In one embodiment, the chitosan may comprise cross linked chitosan. In one embodiment, the hydrogel further comprises a cytokine, a growth factor, a chelator, a cell population, a therapeutic compound, a drug, or any combination thereof.

In some embodiments such a hydrogel biomatrix of this invention may be further enriched for a component as described herein as a consequence of pre-application exposure to an enriched source containing the same. For example, and in some embodiments, prior to implantation, in some embodiments, the hydrogel biomatrix of this invention may be contacted with a subject's biologic fluids, for example, blood or platelet-riched plasma, or lymph, or saliva, as appropriate, which facilitates enrichment of the hydrogel biomatrix with a desired component contained therein.

In one embodiment, the therapeutic compound or drug comprises an anti-inflammatory compound, an anti-infective compound, a pro-angiogenic factor or a combination thereof. In one embodiment, the hydrogel further comprises a chondrogenic support agent, an osteogenic support agent or a combination thereof. In some embodiments, the therapeutic compound or drug comprises an osteoconductive or osteoinductive agent. In some embodiments, the therapeutic compound or drug comprises any combination of embodied agents as herein described.

In some embodiments, the hydrogel biomatrix can be used as a bone filler or bone substitute material. In some embodiments, the hydrogel biomatrix further comprises a bone filler or bone substitute material.

In another embodiment, the present invention provides a kit comprising a hydrogel biomatrix as herein described. In another embodiment, the present invention provides a method of tissue engineering, tissue regeneration or tissue repair in a subject comprising administering to said subject a hydrogel biomatrix as herein described.

In some embodiments, the biomatrix is optionally seeded with a precursor cell, which can participate in said tissue engineering, tissue regeneration or tissue repair.

In one embodiment, the biomatrix is seeded with said precursor cell in culture in the presence of a chelator for a period of time sufficient to seed said precursor cell in said biomatrix.

In another embodiment, the method further comprises inducing or enhancing repair, regeneration or enhancement of formation of cartilage, bone or a combination thereof.

In another embodiment, the subject is a human subject. In another embodiment, the subject is an animal subject.

In another embodiment, the subject is afflicted with a cartilage and/or bone defect or disorder or disease. In another embodiment, the cartilage defect or disorder comprises a full or partial thickness articular cartilage defect; osteochondral defect; a joint defect or a defect resulting from trauma, sports, repetitive stress or osteoarthritis.

In some embodiments, the subject has osteoporosis. In some embodiments, the subject has Paget's disease, fibrous dysplasia or osteodystrophy. In some embodiments, the subject has bone infirmity. In some embodiments, enhancing bone formation comprises healing non-union fractures.

In some embodiments, the method treats a cartilage defect or disorder in said subject.

In some embodiments, the cartilage defect or disorder comprises a full thickness articular cartilage defect; osteoarthritis, osteochondritis dessicans, a joint defect or a defect resulting from trauma, sports, or repetitive stress.

In some embodiments, the methods and materials of this invention are useful in treating bone edema, including subchondral edema and/or bone marrow edema, bone fusions, including foot and ankle fusions, spin fusions, including anterior lumbar interbody spinal fusion, distal radius fusion, fractures, including tibial plateau fractures, and fractures with metaphyseal comminution, distal radious practures, calcaneal fractures, pilon fractures, proximal humerus fractures, tibial fractures and others.

In some embodiments, the methods and materials of this invention are useful in dental applications, such as implant and other reconstructive dental procedures. In some embodiments, the methods and materials of this invention are useful in horizontal and vertical augmentation, sinus lifting, maxillofacial defects, cranial defects, alveolar ridge defects, periodontal defects, and others.

In some embodiments, the methods and materials of this invention are useful in orthopedic applications, including use as orthopedic screws, prostheses and others as will be appreciated by the skilled artisan. In some embodiments, the methods and materials of this invention are useful in applications requiring a filler material, such as gap filler, and in some embodiments, the methods and materials of this invention are useful in applications making use of reinforcing structures, for example as reinforcing screws, grafts, of others. In some embodiments, the methods and materials of this invention are useful in fixation of screws, prosthesis and other structures suitable for such application.

In some embodiments, the methods and materials of this invention are useful in wound healing.

In some embodiments, the methods and materials of this invention are useful in applications in avascular necrosis, cyst or bone tumor treatment, for example, following surgical excision of same.

In some embodiments, the methods and materials of this invention are useful in applications in cranio facial skeletal surgery and skeletal reconstruction applications.

In some embodiments, the marine organism skeletal derivative is aragonite and said method further comprises converting said marine organism skeletal derivative to hydroxyapatite or calcite, wherein such conversion is either full or partial conversion.

In some embodiments, the method further comprises forming a three-dimensional bone filler in sequential cross-sectional layers in accordance with a model of the bone filler, comprising the hydrogel biomatrix.

In some embodiments, such method may encompass three dimensional printing methods, whereby such printing is accomplished via the printing of the hydrogel and marine organism skeletal derivative particles, via methods such as those described in U.S. Pat. Nos. 7,767,132, 6,416,850, and 7,455,804, each of which is fully incorporated by reference herein.

BRIEF DESCRIPTION OF THE DRAWINGS

FIG. 1 provides a series of photographs of implants, which were assessed for their ability to imbibe a biologic fluid, in this case, whole human blood.

FIG. 4A show plugs cut from a larger block, which were assessed for their contact angle characterization. Samples assessed as that of FIG. 4A provided for a contact angle primarily of a smaller degree as herein described. Samples as that in FIG. 4B provided for a larger contact angle as herein described.

FIG. 6 demonstrates the microscopic structure as determined by AFM, of isolated substrates characterized by minimal biologic fluid uptake, versus those characterized by substantial biologic fluid uptake at various magnifications in samples with minimal biologic fluid uptake indicate a much smoother external surface as compared to samples with substantial uptake (FIGS. 6A-6C versus 6D-6F).

DETAILED DESCRIPTION OF THE PRESENT INVENTION

Figure 1C:
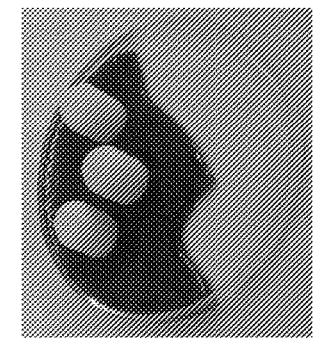
FIGS. 1A-1C show 3 types of patterns of uptake within small coral solid substrate samples, reasonably full uptake as determined by surface color change observation, moderate uptake and minimal uptake, respectively.

Coral, which is comprised of $CaCO_3$ in the crystalline form of calcite or aragonite, has the advantages of allowing fast cellular invasion, adherence, and proliferation. Hydrogels comprising such aragonite or calcite, or conjugated to aragonite or calcite allow for greater diversity of application of the technology in situ, including desirable matrices, which are useful at particular tissue sites, incorporation of other desirable materials, and others known to one skilled in the art.

In one embodiment, the present invention is directed to use of biomatrices comprising hydrogels conjugated to a marine organism skeletal derivative, or hydrogels comprising a marine organism skeletal derivative, optionally seeded with a precursor cell in culture, optionally in the presence of a chelator for various applications, including tissue engineering, regeneration or repair, and biomatrices and kits related thereto. In some embodiments, the present invention is directed to use of biomatrices comprising hydrogels comprising a marine organism skeletal derivative, conjugated to bone or bone-derivatives for such applications.

The invention is directed to biomatrices comprising hydrogels conjugated to or containing suspended therein a marine organism skeletal derivative, or a combination thereof.

In some embodiments, the term "marine organism skeletal derivative-based material" refers to a solid piece or ground material derived from a marine organism, and from a skeletal component of the organism, such as an exoskeleton of the same.

In some embodiments, the term "marine organism skeletal derivative-based material" refers to a corallin-based material. Coral, which is comprised of $CaCO_3$ in the crystalline form of aragonite or calcite has been shown to possess the advantage of supporting fast cellular invasion, adherence and proliferation. Coral has been shown to be an effective substrate for facilitation of the adherence, proliferation and differentiation of mesenchymal stem cells, and ultimate incorporation into cartilage and/or bone tissue. Coral has also been shown to serve as an excellent substrate for promoting adherence and proliferation of a number of other cell types, serving as an excellent support for cell and tissue growth.

The terms "coral" and "aragonite" and "calcite" may be used interchangeably herein.

In some embodiments, the term "marine organism skeletal derivative-based material" refers to a coral or coral derivative. In some embodiments, the term "marine organism skeletal derivative-based material" refers to barnacle or mollusk-derived skeletal material, and in some embodiments, inclusion of nacre is contemplated.

In some embodiments, the hydrogels of this invention contain ground particles derived from coral, suspended in a biocompatible matrix.

In one embodiment, this invention provides a biomatrix comprising a hydrogel conjugated to aragonite or calcite.

In one embodiment, such biomatrices comprising aragonite or calcite provide the shape and support for solidifying/cross linking hydrogels, and/or hydrogel-cell compositions. In some embodiments, the aragonite or calcite has internal pore-like cavities or interstices that are filled by the liquid-hydrogel composition. In some embodiments, cells are recruited to aragonite or calcite and are activated via local release of calcium or other bioactive substance at the site.

In some embodiments, tissues comprising multiple cell types are produced via specific interaction of different cell types with the components of the biomatrices of this invention, e.g. cells interacting with the aragonite or calcite and different cells, or cells at a different stage of differentiation, or both, interacting with the hydrogels, or products contained therein.

In some embodiments, the biomatrix is shaped in the form of the tissue to be grown. For example, the biomatrix can be shaped as a piece of cartilaginous tissue, such as a meniscus for a knee or elbow, a piece of bone to repair a bone defect, an ear, a nose, an internal organ, a ligament, a tendon, the trachea (as a conduit), mandibles, etc. In some embodiments, the aragonite or calcite is shaped either before or after the hydrogel or hydrogel cell composition is conjugated thereto, or in some embodiments, the hydrogel or hydrogel-cell composition fills the aragonite or calcite pore-like cavities.

In some embodiments, the biomatrices of this invention may be formed by a three-dimensional printing process. For example, and in some embodiments, a three-dimensional bone filler may be prepared via a printing process, in sequential cross-sectional layers, in accordance with a model of the desired shape, for example, for the bone filler, or bone scaffold, or other structure, as described herein, printing the components of the hydrogel biomatrices of this invention. In some embodiments, such method may encompass three dimensional printing methods, whereby such printing is accomplished via the printing of the hydrogel and marine organism skeletal derivative particles, via methods such as those described in U.S. Pat. Nos. 7,767,132, 6,416,850, and 7,455,804, each of which is fully incorporated by reference herein.

It will be appreciated by the skilled artisan that any three dimensional printing method, or other method for the assembly of the hydrogel biomatrices of this invention are contemplated and are to be considered as part of this invention.

It will be appreciated that different species of coral vary in terms of their average pore diameter and pore volume and the invention contemplates use of any such coral as a starting material for the preparation of the hydrogels as herein described. As used herein, the tem' "pore volume" refers to volume or open spaces inside the porous marine organism skeletal derivatives used in the hydrogels of this invention. Pore volume is determined by any means known in the art. Porosity can be calculated by standard methods, an example of which is provided further hereinbelow, see for example, Karageorgiou V, Kaplan D. (2005) "Porosity of 3D biomaterial scaffolds and osteogenesis" Biomaterials; 26(27): 5474-91, which is hereby incorporated by reference in its entirety.

It will be appreciated that the term "coral" will refer to a starting material from which aragonite, calcium carbonate, calcite, or hydroxyapatite etc. may be isolated.

The coralline-containing or calcite-containing, etc., hydrogels of this invention may also be used for regeneration, repair and enhancement of formation of bone in a subject, for the treatment of a bone condition, disease or disorder.

This invention provides the unexpected application of the described hydrogels for use, in some embodiments, in a multi-phase arrangement. Such hydrogels are uniquely and superiorly useful in cartilage and/or bone regeneration, repair and enhancement of formation and moreover, that such hydrogels can be prepared and inserted specifically and optimally within cartilage and/or bone in a subject in need thereof, for methods of cartilage and/or bone regeneration, repair and enhancement of formation.

In particular, this invention provides the unexpected advantage in terms of greater incorporation of the hydrogels within the newly developed cartilage, and reduced inflammation, when the hydrogels are prepared and constitute the elements such as those herein described.

In some embodiments, specifically contemplated are multiphasic hydrogel conjugates, comprising a hyrogel phase, comprising a marine organism skeletal derivative biomatrix, for example, as particles suspended in such hydrogel, which hydrogel is further conjugates to a solid phase consisting essentially of a marine organism skeletal derivative biomatrix. In some aspects, a third phase may be constructed, flanking the hyrogel phase comprising the marine organism skeletal derivative biomatrix along with the solid phase. Such third phase may in some embodiments, be comprised of the same elements as the hydrogel, without the marine organism skeletal derivative biomatrix, or in some embodiments, the third phase may comprise smaller particles or a lower concentration of the marine organism skeletal derivative biomatrix.

Unexpectedly, it was found that apical placement of a phase comprising the hydrogel phase, and positioning of the same within the site of repair, or positioning the same slightly under, flush or slightly over the upper limit of the site of defect provides for greater incorporation within the defect site and reduced inflammation associated therewith.

According to this aspect, the porosity and greater rigidity of the more solid phase as compared to the hydrogel phase is more suited for insertion within bone and provides a support, for the repair of bony defects, such as osteochondral defects. The hydrogel conjugates according to this aspect of this invention are therefore, in some embodiments, ideally suited for incorporation within a defect site that spans two different types of tissue, i.e. bone and cartilage.

In some embodiments, the hydrogel may comprise a variety of tissue-promoting, or other desired factors, including nutrients, growth factors, inducers of differentiation or dedifferentiation, products of secretions, immunomodulators, inhibitors of inflammation, regression factors, biologically active compounds which enhance or allow in-growth of the lymphatic network or nerve fibers, and drugs, can be incorporated into the hydrogel.

In one embodiment, the biomatrices, methods and/or kits of this invention employ use of a coral, or aragonite or calcite. In one embodiment, the coral comprise any species, including, inter alia, *Porites, Acropora, Goniopora, Millepora*, or a combination thereof. In another embodiment the solid substrates, processes and/or kits of this invention employ use of nacre, molusc shell, or bone morsels.

In one embodiment, the coral is *Porites Lutea*. In one embodiment, the coral *Acropora grandis*. In another embodiment, the coral is *Millepora dichotoma*.

In one embodiment, the coral is from the *Goniopora* species. In some embodiments, the coral is *Goniopora albiconus, Goniopora burgosi, Goniopora cellulosa, Goniopora ceylon, Goniopora ciliates, Goniopora columna, Goniopora djiboutiensis, Goniopora eclipsensis, Goniopora fruticosa, Goniopora gracilis, Goniopora klunzingeri, Goniopora lobata, Goniopora mauritiensis, Goniopora minor, Goniopora norfolkensis, Goniopora palmensis, Goniopora pandoraensis, Goniopora parvistella, Goniopora pearsoni, Goniopora pendulus, Goniopora planulata, Goniopora polyformis, Goniopora reptans, Goniopora savignyi, Goniopora somaliensis, Goniopora stokes, Goniopora stutchburyi, Goniopora sultani, Goniopora tenella, Goniopora tenuidens* or *Goniopora viridis*.

In another embodiment, the coral is from any one or more of the following species *Favites halicora; Goniastrea retiformis; Acanthastrea echinata; Acanthastrea hemprichi; Acanthastrea ishigakiensis; Acropora aspera; Acropora austera; Acropora* sp. "brown digitate"; *Acropora carduus; Acropora cerealis; Acropora chesterfieldensis; Acropora clathrata; Acropora cophodactyla; Acropora* sp. "danai-like"; *Acropora divaricata; Acropora donei; Acropora echinata; Acropora efflorescens; Acropora gemmifera; globiceps; Acropora granulosa; Acropora* cf *hemprichi; Acropora kosurini; Acropora* cf *loisettae; Acropora longicyathus; Acropora loripes; Acropora* cf *lutkeni; Acropora paniculata; Acropora proximalis; Acropora rudis; Acropora selago; Acropora Acropora* cf *spicifera* as per Veron; *Acropora* cf *spicifera* as per Wallace; *Acropora Acropora valenciennesi; Acropora vaughani; Acropora vermiculata; Astreopora gracilis; Astreopora myriophthalma; Astreopora randalli; Astreopora suggesta; Australomussa rowleyensis; Coscinaraea collumna; Coscinaraea crassa; Cynarina lacrymalis; Distichopora violacea; Echinophyllia echinata; Echinophyllia* cf *echinoporoides; Echinopora gemmacea; Echinopora hirsutissima; Euphyllia ancora; Euphyllia divisa; Euphyllia yaeyamensis; Favia rotundata; Favia truncates; Favites acuticollis; Favities pentagona; Fungia granulosa; Fungia klunzingeri; Fungia mollucensis; Galaxea Goniastrea edwardsi; Goniastea minuta; Hydnophora pilosa; Leptoseris explanata; Leptoseris incrustans; Leptoseris mycetoseroides; Leptoseris scabra; Leptoseris yabei; Lithophyllon undulatum; Lobophyllia hemprichii; Merulina scabricula; Millepora dichotoma; Millepora exaesa; Millipora intricata; Millepora murrayensis; Millipora platyphylla; Monastrea curta; Monastrea colemani; Montipora caliculata; Montipora capitata; Montipora foveolata; Montipora meandrina; Montipora tuberculosa; vietnamensis; Oulophyllia laevis; Oxypora crassispinosa; Oxypora lacera; Pavona bipartita; Pavona venosa; Pectinia alcicornis; Pectinia paeonea; Platygyra acuta; pini; Platygyra* sp "green"; *Platygyra verweyi; Podabacia* cf *lanakensis; Porites annae; Porites cylindrica; Porites evermanni; Porites monticulosa; Psammocora digitata; Psammocora explanulata; Psammocora haimeana; Psammocora superficialis; dentata; Seriatopora caliendrum; Stylocoeniella armata; Stylocoeniella guentheri*; sp.; *Tubipora musica; Turbinaria stellulata*; or any coral known in the art, or a thereof.

In another embodiment, derivatives of marine animals—such as coral, sponges, moluscs shells and other related organisms may be used in the solid substrates, methods and/or kits of this invention may be *Madreporaria, Helioporida* of the order Coenothecalia, *Tubipora* of the order Stolonifera, *Millepora* of the order Milleporina, or others known in the art. In some embodiments, coral for use in the hydrogels, methods and/or kits of this invention may comprise scleractinian coral, including in some embodiments, *Goniopora* and others. In some embodiments, coral for use in the substrates, methods and/or kits of this invention may comprise Alveoppora. In some embodiments, coral for use in the substrates, methods and/or kits of this invention may comprise bamboo corals, including in some embodiments, coral from the family Isididae, genera *Keratoisis, Isidella*, and others. In another embodiment, coral for use in the biomatrices, methods and/or kits of this invention may be Madreporaria, Helioporida of the order Coenothecalia, *Tubipora* of the order Stolonifera, *Millepora* of the order Milleporina, or others known in the art.

In some embodiments, the coral for use in the preparation of the solid substrates of this invention may be processed by any means known in the art, for example, as described in PCT International Application Publication Number WO 2009/066283, PCT International Application Publication Number WO 2010/058400, PCT International Application Publication Number WO 2010/146574 and PCT International Application Publication Number WO 2010/146574, each of which is fully incorporated by reference herein, in its entirety.

In one embodiment, the size of coral-containing hydrogels may be any size that would be useful for the purposes of the present invention, as would be known to one of skill in the Art depending on the purpose. For example and in one embodiment, the coral-containing hydrogels may be substantially the same size as the structure it is meant to replace, while in another embodiment, the coral-containing hydrogels may be the size of a bone fissure or fracture such that it may be placed therein to enhance bone formation in a discrete location.

It is to be noted that the usefulness for coralline substrates for promoting tissue growth such as cartilage and bone has been previously shown. Surprisingly, it has now been found that while numerous coral-based substrates isolated can be used for such repair, consistent and superior function was found when the substrates were chosen specifically for their enhanced spontaneous uptake of biologic fluids. Added benefit can therefore also be derived from incorporating such substrates within hydrogels for use in the therapeutic and supportive applications as described herein.

Surprisingly, it was found, not only that coral based materials can be an effective material for promoting cell and tissue growth and/or restored function, but that the spontaneous fluid absorptive characteristics of the selected sample of coral for use in the same provided even greater activity in this regard.

Without being bound by theory, and representing non-limiting embodiments of the substrates, processes and applications of this invention, specific selection of marine organism skeletal derivative-based solid substrates characterized by the desired specific fluid uptake capacity value of at least 75%, or specific selection of organism skeletal derivative-based solid substrates characterized by having a contact angle value of less than 60 degrees, when in contact with a fluid, may select for a sample whose vascularization is enhanced, or in some embodiments, whose access to lymph is enhanced, or in some embodiments, whose absorptive capacity heralds an affinity for extracellular matrix-associated materials, or in some embodiments, whose absorptive capacity heralds an affinity for cellular attraction including extravasation from proximal vessels.

Furthermore, and without being bound by theory, and representing non-limiting embodiments of the hydrogel biomatrices, processes and applications of this invention, specific components of the hydrogels may be tailored for a particular and site/patient/therapy application, including in consideration of the desired specific site or location of implantation, consideration of the desired specific density, strength and viscosity of the implanted material.

In some embodiments, the hydrogel platform provides for the additional therapeutic potential afforded by the incorporation therewithin and ultimate localized release of factors, which contribute to a desired effect. For example, and in some embodiments, altering the particle size distribution of the marine organism skeletal derivative incorporated therewithin and/or specific choice of/altering hydrogel viscosity or density of the biomaterix can provide added therapeutic potential, which advantages are readily apparent to the skilled artisan.

In some embodiments, the hydrogel platform provides for the additional therapeutic potential afforded by providing a platform for personalized care, tailored to a specific need, genetic makeup, lifestyle preference etc., to a given patient, including the possibility for considerations of application of the same to specific implantation sites to better treat specific indications.

In some embodiments, the hydrogel platform provides for the additional therapeutic potential afforded by three dimension printing construction, providing yet another means to create a biomatrix idealized in fit in terms of its size, shape and/or porosity.

In some embodiments, the hydrogel platform provides for the additional therapeutic potential afforded by altering the consistency of the hydrogel biomatrix, to resemble a paste, putty, or cement, and in some embodiments, to create an injectable or press fitted formulation.

In some embodiments, the hydrogel platform provides for the additional therapeutic potential afforded by the ability to further incorporate bone particles therewithin, in addition to the marine organism skeletal derivative. According to this aspect, and in some embodiments, incorporation of both original bone material and marine organism skeletal derivative promotes potential "seeding" of the marine organism skeletal derivative elements, due to local factors provided by the recognition/presence of bone. In some embodiments, the incorporation of both results in a synergistic effect. In some embodiments, such bone material may include bone from any source, such as, for example, cadaveric allograft, bone particles or demineralized bone matrices, xenograft particles as well as autologous, syngeneic or haplotype-matched bone.

It is to be understood that any of these mechanisms, and others, may account for the phenomenon of enhanced cell or tissue growth or restored function, and that any such mechanism associated with the application of an optimized marine organism skeletal derivative—containing hydrogel for promoting cell or tissue growth or restored function characterized by a specific fluid uptake capacity value of at least 75% is to be understood as being part of this invention.

In some embodiments, samples thus processed and found to be characterized by a specific fluid uptake capacity value of at least 75%, or specific selection of organism skeletal derivative-based solid substrates characterized by having a contact angle value of less than 60 degrees, when in contact with a fluid may then be used for the isolation of proximally located regions of a section from which such sample was taken, which samples can then be reliably used and considered as being optimized in accordance with the processes of this invention. In some embodiments, with regard to coral-based samples, such regions may include the entire annual growth ring region within the coral from which the sample was derived.

In some embodiments, samples thus processed and found to be characterized by a specific fluid uptake capacity value of at least 75%, or specific selection of organism skeletal derivative-based solid substrates characterized by having a contact angle value of less than 60 degrees, when in contact with a fluid, may then be dried fully and utilized for preparation of the hydrogels of this invention, for ultimate implantation into a subject or for use as an ex-vivo substrate for cell or tissue growth for subsequent implantation.

In some embodiments, the marine organism skeletal derivatives for incorporation within the hydrogel biomatrices of this invention will include a solid substrate for promoting cell or tissue growth or restored function, which solid substrate comprises a marine organism skeletal derivative and is characterized by substantial surface roughness (Ra) as measured by scanning electron microscopy or atomic force microscopy. According to this aspect, and in some embodiments, the therapeutic potential afforded by the incorporation of such derivatives therewithin will be the same or comparable to those described hereinabove in terms of the material's specific uptake capacity or contact angle value.

In some embodiments, such biomatrices will comprise components with enhanced surface area, due to the different surfaces noted in the specific marine skeletal derivatives used in accordance with this invention.

In some embodiments, when the sample is utilized in vivo in subsequent applications, in some aspects, the sample is first contacted with autologous biological fluids or materials from the host prior to implantation into the same, verifying the observed enhanced fluid uptake phenotype as herein described.

In other embodiments the substrate may be a mixture of several marine originated materials or a mixture of bone and coral granules or cartilage and coral granules. In some embodiments, the solid substrate may be a composite material comprised of multiple samples of the marine organism skeletal derivatives as herein described.

In one embodiment, coral is washed, bleached, frozen, dried, or a combination thereof prior to seeding with precursor cells.

In some embodiments, the aragonite-based coral biomatrix is thermically converted to calcite via known methods. Calcite polymorphs of calcium carbonate from natural limestone have been described and in vitro transformation of calcite by heating aragonite isolated from natural coral, has been described, as well [Fujita Y, Yamamuro T, Nakamura T, Kotani S, Ohtsuki C, Kokubo T. J Bimed Mater Res. 1991 August; 25(8):991-1003; Fricain J C, Bareille R, Ulysse F, Dupuy B, Amedee J. J. Biomed Mater Res. 1998 October; 42(1):96-102]. The transition to calcite can be performed by, for example, heating aragonite to 300° C. for 2 h under vacuum conditions [see for example Liu M and Yung A, Transformation kinetics of polycrystalline aragonite to calcite: new experimental data, modeling and implications. J. Contributions to mineralogy and petrology, 114(4), 1993: 465-478].

Calcite formation may be confirmed by SEM and FTIR analysis [see for example, La Russa M F, Ruffolo S A, Barone G, Crisci G M, Mazzoleni P, Pezzino A. The Use of FTIR and Micro-FTIR Spectroscopy: An Example of Application to Cultural Heritage *International Journal of Spectroscopy,* 2009(2009):1-5].

The calcite may, in some embodiments, be any crystalline or amorphous form and derived from, inter alia, a coral or barnacle species, such as from any Cirripedia, Crustacea, for example, *Tetraclita rufotincta.*

In one embodiment, coral is washed, bleached, frozen, dried, exposed to electrical forces, magnetic forces or ultrasound waves or microwaves or electromagnetic radiation or high or low pressure or a combination thereof prior to use thereof.

In some embodiments, the purification of coral for use in the preparation of the hydrogels and kits of this invention is by any appropriate means. In some embodiments, such process may comprise the steps of:

contacting solid aragonite of a desired size and shape with a solution comprising an oxidizing agent; and washing and drying said solid aragonite whereby one or each of said steps is conducted under applied negative pressure.

According to this aspect, and in some embodiments, the applied negative pressure ranges between about 0.2 to 0.00001 Bar, or in some embodiments, the applied negative pressure ranges between 0.4 to 0.0000001 Bar.

According to this aspect, and in some embodiments, the oxidizing agent for use in the processes of this invention may be any suitable oxidizing agent, which facilitates the removal of organic debris from coralline-based solid substrates.

In some embodiments, the oxidizing agent may include, inter alia, potassium nitrate (KNO3), hypochlorite and other hypohalite compounds, iodine and other halogens, chlorite, chlorate, perchlorate, permanganate salts, ammonium cerium(IV) nitrate, hexavalent chromium compounds, pyridinium chlorochromate (PCC), and chromate/dichromate compounds, peroxide compounds, sulfoxides, persulfuric acid, or nitric acid, acetone, ammonium peroxydisulfate, 1,4-benzoquinone, N-tert-butylbenzensulfinilmidoyl, chloride, tert-butyl hydroperoxide, tert-butyl hypochlorite, 3-chloroperoxybenzoic acid, meta-chloroperbenzoic acid, cumene hydroperoxide, dimethyl sulfoxide, hydrogen peroxide, manganese oxide, meta-chloroperbenzoic acid, N-methylmorpholine-N-oxide, methyltrioxorhenium (MTO), oxalyl chloride, N-tert-butylbenzenesulfinimidoyl chloride, oxone, oxygen, ozone, peracetic acid, periodic acid, peroxy acid, pivaldehyde, potassium permanganate, potassium peroxydisulfate, potassium peroximonosulfate, 2-propanone, sodium chlorite, sodium percarbonate, sodium periodate, styrene, trichloroisocyanuric acid (TCCA), 2,2,6, 6-tetramethylpiperidinyloxy TEMPO, tert-butyl hydroperoxide, tert-butyl hypochlorite, tetrabutylammonium peroxydisulphate, trimethylacetaldehyde. In some embodiments, the oxidizing agent is sodium hypochlorite.

According to this aspect, and in some embodiments, the process comprises conducting said contacting under mildly acidic conditions.

According to this aspect, and in some embodiments, the process comprises subjecting the solid aragonite to a temperature of at least 275° C. under applied negative pressure.

According to this aspect of the invention, the process comprises contacting the aragonite with an oxidizing agent under applied negative pressure, washing and drying the aragonite applied negative pressure, or both steps are conducted under applied negative pressure. The applied negative pressure ranges between 0.2 to 0.00001 Bar, or in some embodiments, between about 0.4 to 0.0000001 Bar, according to this aspect of the invention.

In some embodiments, the invention contemplates use of calcite obtained from aragonite, as well. Any method for conversion of aragonite to calcite as known in the art may be used to prepare calcite solid substrates of this invention. In some embodiments, the invention contemplates use of hydroxyapatite obtained from aragonite, as well. In some embodiments, coral—may be converted partially or fully into hydroxyapatite or calcite by known methods.

In another embodiment, biomatrices and/or kits and/or their use in accordance with the present invention are produced according to a process comprising washing naturally occurring aragonite or calcite particles with water to desalinate it, then purifying and drying the desalinated aragonite or calcite.

In some embodiments, the process comprises grinding the aragonite or calcite into small particles, which in one embodiment comprise particles of 1-10 microns.

In some embodiments the grinding may be conducted prior to or following the purification/washing of the marine organism skeletal derivative material.

In another embodiment, aragonite or calcite is ground into particles of 1-5, 1-20, 1-50, 1-100, 5-10, 10-15, 15-20, 10-50, 10-100, 20-100, 50-100, 20-400, 100-400, 75-250, 150-400, 200-400 or 300-400 microns. In other embodiments, the a marine organism skeletal derivatives are ground into particles of 20-50, 20-100, 40-150, 50-250, 45-200, 30-80, 30-100, 60-300, 50-500, 90-400, 100-400, 75-250, 150-400, 200-400 or 300-400 nanometers.

In another embodiment, the biomatrices and/or kits and/or their use in accordance with the present invention include/ make use of macroparticles, which macroparticles may be of a size ranging between 50-200, 100-300, 200-500, 300, 800, 500-1000 micrometers, and 0.1-0.2, 0.5-2, 0.3-0.7, 0.4-1, 0.5-1.5, 1-2, 1.5-3, 2-3, 3-5, 1-5, 2-10, 5-20, 15-30, 20-40, and 30-50 millimeters.

In another embodiment, the biomatrices and/or kits and/or their use in accordance with the present invention include/ make use of macroparticles, which macroparticles may be of a size ranging between 50-200, 100-300, 200-500, 300, 800, 500-1000 millimeters, and 0.1-0.2, 0.5-2, 0.3-0.7, 0.4-1, 0.5-1.5, 1-2 centimeters.

In another embodiment, aragonite or calcite may be ground to the desired size by known methods, for example by standard grinding apparatus, use of appropriate mesh sizes, which may also include temperature mediated effects to achieve the desired size.

The thus obtained finely divided aragonite or calcite particles are highly porous. The so obtained aragonite or calcite particles may be suspended in water or saline and then incorporated in a gel or suspended directly in a gel as herein described to form the biomatrices of this invention. Aragonite or calcite may be similarly reconstituted, and kits providing the particles and additional biomatrix components for assembly/reconstitution of same are contemplated as well, and to be considered as part of this invention, as will be appreciated by one skilled in the art.

Fine powders of the aragonite or calcite particles may be formulated as granules, emulsions, suspension concentrates, paste, putty etc. Granules may be fabricated using size reduction equipment such as a diamond saw, jaw crushing, milling, or manufactured by agglomeration or impregnation techniques. These particles may be further processed by using size exclusion techniques such as sieving. The aragonite or calcite may then be suspended in gels, emulsions, suspension concentrates, and/or hydrogels as herein described or incorporated in the biomatrices in other means, as appreciated by one skilled in the art and a combination thereof.

The biomatrices and/or kits of the present invention may also contain other ingredients, for example, various nutrients such as vitamins (vitamins A, B, C, E, F, etc.), sugars (glucose, fructose, sucrose, maltose, or the like).

In some embodiments, the biomatrices and/or kits and/or their use in accordance with the present invention comprise between 35-90% w/w of the composition being aragonite or calcite.

In some embodiments, the biomatrices, methods and/or kits of this invention make use of aragonite or calcite conjugated to a hydrogel, or in some embodiments, the biomatrices, methods and/or kits of this invention make use of hydrogels comprising aragonite or calcite, for example coral macroparticles, microparticles or nanoparticles suspended or otherwise contained therein.

In some embodiments, the hydrogels used to practice this invention are biocompatible and biodegradable. Furthermore in some embodiments, these hydrogels solidify in vivo, e.g., in a time period of between a 1-20 seconds, 10-60 seconds, 30-180 seconds, 2-5 minutes, 3-10 minutes, 5-25 minutes, 15-60 minutes, 30 minutes-5 hours after being delivered. These hydrogels may contain aragonite or calcite. These structures are capable of sustaining living cells.

Examples of different hydrogels suitable for practicing this invention, include, but are not limited to: (1) temperature dependent hydrogels that cross linked or set at body temperature, e.g., PLURONICS™, Gelatin, PEG based gels such as polyethylene glycol diacrylate; (2) hydrogels cross-linked by ions, e.g., sodium alginate, chitosan, collagen and hyaluronic acid; (3) hydrogels set by exposure to either visible or ultraviolet light, e.g., polyethylene glycol, polylactic acid copolymers with acrylate end groups; and (4) hydrogels that are set or solidified upon a change in pH, e.g., TETRONICS™ (5) hydrogels that set in a physiological manner such as fibrinogen and thrombin using biological enzymes or similar factors such as factor XIII (6) viscous polymers such as carboxy methyl cellulose, poly alpha hydroxyl acids and their copolymers.

In some embodiments, the biomatrices of this invention may incorporate naturally viscous polymers, such as gelatin, which require no cross-linking to achieve such viscosity.

In some embodiments, the biomatrices of this invention may incorporate materials, whose viscosity can be increased by cross-linking of the same. According to this aspect, and in some embodiments, such cross linking may be achieved prior to packaging, and present in a ready made product. In other embodiments, kits of this invention may include a separately contained cross linking agent or agents, and instructions for optimal use of the same to effect cross linking at time closer to use. In some embodiments, according to this aspect, a cross linking agent may be applied in situ, to promote cross linking of the components of the biomatrix at the time of or proximal to the time of implantation. In some embodiments, according to this aspect, a cross linking agent may be incorporated within the hydrogel matrices of this invention and then activated in situ, to promote cross linking of the components of the biomatrix at the time of or proximal to the time of implantation.

It will be apparent to the skilled artisan that any known biocompatible cross-linking agent may be utilized to achieve the cross-linking described herein, which will not be negative as a consequence of the type of bond formed for the same.

Examples of materials that can be used to form these different hydrogels include polysaccharides such as alginate, polyphosphazenes, and polyacrylates, which are cross-linked ionically, or block copolymers such as PLURONICS™ (also known as POLOXAMERS™), which are poly(oxyethylene)-poly(oxypropylene) block polymers that may solidify in response to changes in temperature, or TETRONICS™ (also known as POLOXAMINES™), which are poly(oxyethylene)-poly(oxypropylene) block polymers of ethylene diamine solidified by changes in pH. Other examples include Poly-HEMA (poly 2 hydroxylthyl methacrylate), which is perhaps the most widely used hydrogel, in which the degree of cross linking may be so selected in order to influence the resulting properties of the hydrogel.

Ionic Hydrogels

Ionic polysaccharides, such as alginates or chitosan, and or hyaluronic acid can be used/comprise the biomatrices of this invention, in some. In one embodiment, the hydrogel is produced by cross-linking the anionic salt of alginic acid, a carbohydrate polymer isolated from seaweed, with ions, such as calcium cations. The strength of the hydrogel increases with either increasing concentrations of calcium ions or alginate. For example, U.S. Pat. No. 4,352,883 describes the ionic cross-linking of alginate with divalent cations, in water, at room temperature, to form a hydrogel matrix.

In some embodiments, a desired population of cells, such as stem and/or precursor cells are mixed with an alginate solution, the solution is mixed with the aragonite or calcite particles and then cross linked and solidifies in a short time due to the presence of physiological concentrations of calcium ions, or local release of calcium from aragonite or calcite supports by the administered cells. In some embodiments, the desired population of cells is applied to the biomatrix after it has been constructed.

In some embodiments, polymers comprising the hydrogels are at least partially soluble in aqueous solutions, e.g., water, or aqueous alcohol solutions that have charged side groups, or a monovalent ionic salt thereof. There are many examples of polymers with acidic side groups that can be reacted with cations, e.g., poly(phosphazenes), poly(acrylic acids), and poly(methacrylic acids). Examples of acidic groups include carboxylic acid groups, sulfonic acid groups, and halogenated (preferably fluorinated) alcohol groups. Examples of polymers with basic side groups that can react with anions are poly(vinyl amines), poly(vinyl pyridine), and poly(vinyl imidazole).

Polyphosphazenes are polymers with backbones consisting of nitrogen and phosphorous atoms separated by alternating single and double bonds. Each phosphorous atom is covalently bonded to two side chains. Polyphosphazenes that can be used have a majority of side chains that are acidic and capable of forming salt bridges with di- or trivalent cations. Examples of acidic side chains are carboxylic acid groups and sulfonic acid groups.

Bioerodible polyphosphazenes have at least two differing types of side chains, acidic side groups capable of forming salt bridges with multivalent cations, and side groups that hydrolyze under in vivo conditions, e.g., imidazole groups, amino acid esters, glycerol, and glucosyl. Bioerodible or biodegradable polymers, i.e., polymers that dissolve or degrade within a period that is acceptable in the desired application (usually in vivo therapy), will degrade in less than about five years and most preferably in less than about one year, once exposed to a physiological solution of pH 6-8 having a temperature of between about 25° C. and 38° C. Hydrolysis of the side chain results in erosion of the polymer. Examples of hydrolyzing side chains are unsubstituted and substituted imidazoles and amino acid esters in which the side chain is bonded to the phosphorous atom through an amino linkage.

Methods for synthesis and the analysis of various types of polyphosphazenes are described in U.S. Pat. Nos. 4,440,921, 4,495,174, and 4,880,622. Methods for the synthesis of the other polymers described above are known to those skilled in the art. See, for example Concise Encyclopedia of Polymer Science and Engineering, J. I. Kroschwitz, editor (John Wiley and Sons, New York, N.Y., 1990). Many polymers, such as poly(acrylic acid), alginates, and PLURONICS™, are commercially available.

Water soluble polymers with charged side groups are cross-linked by reacting the polymer with an aqueous solution containing multivalent ions of the opposite charge, either multivalent cations if the polymer has acidic side groups, or multivalent anions if the polymer has basic side groups. Cations for cross-linking the polymers with acidic side groups to form a hydrogel include divalent and trivalent cations such as copper, calcium, aluminum, magnesium, and strontium. Aqueous solutions of the salts of these cations are added to the polymers to form soft, highly swollen hydrogels.

Anions for cross-linking the polymers to form a hydrogel include divalent and trivalent anions such as low molecular weight dicarboxylate ions, terepthalate ions, sulfate ions, and carbonate ions. Aqueous solutions of the salts of these anions are added to the polymers to form soft, highly swollen hydrogels, as described with respect to cations.

For purposes of preventing the passage of antibodies into the hydrogel, but allowing the entry of nutrients, a useful polymer size in the hydrogel is in the range of between 1,000-20,000 kD. Smaller polymers result in gels of higher density with smaller pores.

Temperature-Dependent Hydrogels

Temperature-dependent, or thermosensitive, hydrogels can be used in the biomatrices, kits and/or methods of the invention, in some embodiments. These hydrogels have so-called "reverse gelation" properties, i.e., they are liquids at or below room temperature, and gel when warmed to higher temperatures, e.g., body temperature. In some embodiments, these hydrogels can be easily applied at or below room temperature as a liquid and automatically form a semi-solid gel when warmed to body temperature. In some embodiments, the coral or the biomatrices of this invention are first implanted into a patient, and then filled with a hydrogel or hydrogel-cell composition, as herein described, in some embodiments. In some embodiments, such hydrogels may comprise aragonite or calcite particles, as well, in addition to being adhered or filling a aragonite or calcite scaffold.

It is to be understood that any of the biomatrices as herein described may comprise aragonite or calcite conjugated to a hydrogel, the biomatrices may comprise a hydrogel within pores of the aragonite or calcite structure, or the biomatrices may comprise hydrogels comprising aragonite or calcite particles, or combinations thereof, for example, any of the hydrogels utilized in the former biomatrices may also further comprise aragonite or calcite particles. All of these comprise embodiments of what is meant by a biomatrix of this invention.

Examples of such temperature-dependent hydrogels are PLURONICS™ (BASF-Wyandotte), such as polyoxyethylene-polyoxypropylene F-108, F-68, and F-127, poly (N-isopropylacrylamide), and N-isopropylacrylamide copolymers. These copolymers can be manipulated by standard techniques to affect their physical properties such as porosity, rate of degradation, transition temperature, and degree of rigidity. For example, the addition of low molecular weight saccharides in the presence and absence of salts affects the lower critical solution temperature (LCST) of typical thermosensitive polymers. In addition, when these gels are prepared at concentrations ranging between 5 and 25% (WN) by dispersion at 4° C., the viscosity and the gel-sol transition temperature are affected, the gel-sol transition temperature being inversely related to the concentration. These gels have diffusion characteristics capable of allowing cells to survive and be nourished.

U.S. Pat. No. 4,188,373 describes using PLURONIC™ polyols in aqueous compositions to provide thermal gelling aqueous systems. U.S. Pat. Nos. 4,474,751, '752, '753, and 4,478,822 describe drug delivery systems which utilize thermosetting polyoxyalkylene gels; with these systems, both the gel transition temperature and/or the rigidity of the gel can be modified by adjustment of the pH and/or the ionic strength, as well as by the concentration of the polymer, or combinations thereof.

pH-Dependent Hydrogels

Other hydrogels suitable for use in the biomatrices, kits and/or methods of the invention are pH-dependent. These hydrogels are liquids at, below, or above specific pH values, and gel when exposed to specific pHs, e.g., 7.35 to 7.45, the normal pH range of extracellular fluids within the human body. Thus, these hydrogels can be easily delivered to an implanted support structure as a liquid and automatically form a semi-solid gel when exposed to body pH. Examples of such pH-dependent hydrogels are TETRONICS™ (BASF-Wyandotte) polyoxyethylene-polyoxypropylene polymers of ethylene diamine, poly(diethyl aminoethyl methacrylate-g-ethylene glycol), and poly(2-hydroxymethyl methacrylate). These copolymers can be manipulated by standard techniques to affect their physical properties.

Light Solidified Hydrogels

Other hydrogels that can be used in the biomatrices, kits and/or methods of the invention are solidified or cross linked using either visible or ultraviolet light. These hydrogels are made of macromers including a water soluble region, a biodegradable region, and at least two polymerizable regions as described in U.S. Pat. No. 5,410,016. For example, the hydrogel can begin with a biodegradable, polymerizable macromer including a core, an extension on each end of the core, and an end cap on each extension. The core is a hydrophilic polymer, the extensions are biodegradable polymers, and the end caps are oligomers capable of cross-linking the macromers upon exposure to visible or ultraviolet light, e.g., long wavelength ultraviolet light.

Examples of such light crosslinking hydrogels include polyethylene oxide block copolymers, polyethylene glycol polylactic acid copolymers with acrylate end groups, and polyethylene glycol-glycolide copolymer capped by an acrylate at both ends. As with the PLURONIC™ hydrogels, the copolymers comprising these hydrogels can be manipulated by standard techniques to modify their physical properties such as rate of degradation, differences in crystallinity, and degree of rigidity.

In some embodiments, the following hydrogel components are specifically contemplated: Calcium Sulfate, Fibrinogen glue, Collagen type I, Calcium Phosphate, Crosslinked Alginate, Sodium hyaluronate, Poly Methyl Methacrylate, PEG diacrylate, Gelatin, Crosslinked Collagen, Carboxyl methyl Cellulose (CMC), Hypromellose, Glycerin, poly(D,L-lactide-co-glycolide) (PLGA) in any combination thereof. In some embodiments, the following hydrogel components are specifically contemplated: Collagen, Fibrin and hyaluronic acid; Collagen and Calcium Phosphate; PEG diacrylate and Collagen and hyaluronic acid. A hydrogel for each of such matrices is prepared, containing or conjugated to a marine organism skeletal derivative, as described.

In some embodiments, the biomatrices of this invention comprise or incorporate a gel with the aragonite or calcite, for example, conjugation thereto, or in some embodiments, penetration within the coral, such as occupying the pores of the aragonite or calcite, or in some embodiments, the biomatrices comprise a gel comprising suspended aragonite or calcite particles.

In some embodiments, the term "gel" encompasses its ordinary meaning in the art. In one embodiment, the term "gel" refers to a composition comprising a viscous polymer having a fluidity at room temperature between that of a liquid and a solid. In some embodiments, the term "gel" refers to a solid or semisolid colloid system formed of a solid continuous phase and a liquid phase (either discontinuous or continuous or mixed), which, in some embodiments, can be identified by its outward gelatinous appearance, and/or exhibits properties of a solid such as plasticity, elasticity, or rigidity. In some embodiments, the liquid phase can be a 'dispersed' phase, or in other embodiments, the continuous phase. In some embodiments, the gelling component (solid phase) is lipophilic and present in concentrations of less than 10, or in another embodiment, 15, or in another embodiment 20, or in another embodiment, 25, or in another embodiment, 30, or in another embodiment, 40 percent. In some embodiments, the term "gel" may encompass a silica gel, an aluminosilicate gel or other materials, which are primarily solid and/or particulate, microspheroidal, spheroidal, etc., or described with descriptive properties, terms, or expressions which indicates a two-phase system, such as, pore volume, pore diameter, surface area. In one embodiment, the gel is a hydrogel, or in another embodiment, the gel comprises polymers dispersed in solvents other than water or aqueous solutions.

In some embodiments, the hydrogel biomatrices of this invention include those characterized by a high viscosity, such as, for example, found in a paste or putty. In some embodiments, the hydrogel biomatrices of this invention include a matrix, which can be solidified to form cement, as well. In some embodiments, such solidification may be accomplished coincident with or soon after application to a defect/wound/fracture site.

In one embodiment, the gel comprises a polymer, which may comprise, inter-alia, poly (pyranose), poly(hydroxyl acid), poly(lactone), poly (amino acid), poly(anhydride), poly (urethane), poly (orthoester), poly (phosphazine), poly (phosphoester) or poly (lactic-co-glycolic) acid, poly(ether ester)s, synthetic poly(amino acids), polycarbonates, poly (hydroxyalkanoate)s, and poly(ε-caprolactone)s.

In one embodiment, the polymer is a synthetic polymer, or in another embodiment, the polymer is a natural polymer. In one embodiment, the polymer is a poly(cianoacrylate), poly(alkyl-cianoacrylate), poly(ketal), poly(caprolactone), poly(acetal), poly(α-hydroxy-ester), poly(β-hydroxy-ester), poly(hydroxyl-alkanoate), poly(propylene-fumarate), poly (imino-carbonate), poly(ester), poly(ethers), poly(carbonates), poly(amide), poly(siloxane), poly(silane), poly(sulfide), poly(imides), poly(urea), poly(amide-enamine), poly (organic acid), poly(electrolytes), poly(p-dioxanone), poly (olefin), poloxamer, inorganic or organomatallic polymers, elastomer, or any of their derivatives, or a copolymer obtained by a combination thereof.

In one embodiment, the polymer comprises poly(D,L-lactide-co-glycolide) (PLGA). In another embodiment, the polymer comprises poly(D,L-lactide) (PLA). In another embodiment, the polymer comprises poly(D,L-glycolide) (PGA). In one embodiment, the polymer comprises a glycosaminoglycan.

In one embodiment, the polymer may comprise proteins such as zein, modified zein, casein, gelatin, gluten, serum albumin, collagen, actin, α-fetoprotein, globulin, macroglobulin, cohesin, laminin, fibronectin, fibrinogen, osteocalcin, osteopontin, osteoprotegerin, or others, as will be appreciated by one skilled in the art. In another embodiment, the polymer may comprise cyclic sugars, cyclodextrins, synthetic derivatives of cyclodextrins, glycolipids, glycosaminoglycans, oligosaccharide, polysaccharides such as alginate, carrageenan ($\chi$, $\lambda$, $\mu$, $\kappa$), chitosane, celluloses, condroitin sulfate, curdlan, dextrans, elsinan, furcellran, galactomannan, gellan, glycogen, arabic gum, guar gum, hemicellulose, inulin, karaya gum, levan, pectin, pollulan, pullulane, prophyran, scleroglucan, starch, tragacanth gum, welan, xanthan, xylan, xyloglucan, hyaluronic acid, chitin, poly(3-hydroxyalkanoate)s, such as poly(β-hydroxybutyrate), poly(3-hydroxyoctanoate) or poly(3-hydroxyfatty acids). In another embodiment, the polymer may comprise chemical derivatives thereof (substitutions, additions, and elimination of chemical groups, for example, alkyl, alkylene, hydroxylations, oxidations, and other modifications routinely made by those skilled in the art), blends of, e.g. proteins or carbohydrates alone or in combination with synthetic polymers, or any combination thereof.

In one embodiment, the polymer comprises synthetically modified natural polymers, and may include cellulose derivatives such as alkyl celluloses, carboxy methyl cellulose, hydroxyalkyl celluloses, cellulose ethers, cellulose esters, nitrocelluloses, and chitosan. Examples of suitable cellulose derivatives include methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxymethyl cellulose, cellulose triacetate and cellulose sulfate sodium salt or any combination thereof.

In one embodiment, the polymer comprises synthetic degradable polymers, which may include, but are not limited to polyhydroxy acids, such as poly(lactide)s, poly(glycolide)s and copolymers thereof; poly(ethylene terephthalate); poly(hydroxybutyric acid); poly(hydroxyvaleric acid); poly[lactide-co-(ε-caprolactone)]; poly[glycolide-co(ε-caprolactone)]; poly(carbonate)s, poly(pseudo amino acids); poly(amino acids); poly(hydroxyalkanoate)s; poly(anhydrides); poly(ortho ester)s; and blends and copolymers thereof.

In one embodiment, the polymer comprises a bioerodible polymer such as poly(lactide-co-glycolide)s, poly(anhydride)s, and poly(orthoester)s, which have carboxylic groups exposed on the external surface as the smooth surface of the polymer erodes, which may also be used. In one embodiment, the polymer contains labile bonds, such as polyanhydrides and polyesters.

In one embodiment, the polymer is biodegradable. In one embodiment, the term "biodegradable polymer" refers to a material, which is degraded in the biological environment of the cell or subject in which it is found. In one embodiment, the biodegradable polymer undergoes degradation, during which, acidic products, or in another embodiment, basic products are released. In one embodiment, bio-degradation involves the degradation of the polymer into its component subunits, via, for example, digestion, by a biochemical process or enzymatic degradation. In one embodiment, biodegradation may involve cleavage of bonds (whether covalent or otherwise) in the polymer backbone. In another embodiment, biodegradation may involve cleavage of a bond (whether covalent or otherwise) internal to a side-chain or one that connects a side chain to the polymer backbone.

In one embodiment, the biomatrices of this invention comprise aragonite or calcite covalently associated with the gel as described herein, or in another embodiment, the aragonite or calcite forms a physical interaction with the gel.

In one embodiment, the aragonite or calcite is covalently associated with the gel via the use of a cross-linking agent. In one embodiment, the term "cross-linking agent" refers to an agent which facilitates the formation of a covalent bond between 2 atoms. In one embodiment, the cross-linking agent is a zero-length cross-linking agent.

In one embodiment, the cross-linking agent is (1 ethyl 3-(3dimethyl aminopropyl)carbodiimide (EDAC), N-Sulfo-hydroxy succinamide (Sulfo NHS), 5-iodopyrimidines, N-carbalkoxydihydroquinolines, pyrroloquinolinequinones, or a combination thereof.

In one embodiment, the cross-linking agent is a homobi-functional cross-linker, such as, for example, a N-hydroxy-succinimide ester (e.g. disuccinimidyl suberate or dithiobis (succinimidylpropionate), homobifunctional imidoester (e.g. dimethyladipimidate or dimethyl pimelimidate), sulf-hydryl-reactive crosslinker (e.g. 1,4-di-[3'-(2'-pyridyldithio) propionamido]butane), difluorobenzene derivative (e.g. 1,5-difluoro-2,4-dinitrobenzene), aldehyde (e.g. formaldehyde, glutaraldehyde), bis-epoxide (e.g. 1,4-butanediol diglycidyl ether), hydrazide (e.g. adipic acid dihydrazide), bis-diazo-nium derivative (e.g. o-tolidine), bis-alkylhalide, or a combination thereof.

In one embodiment, the cross-linking agent is a hetero-bifunctional cross-linker, such as, for example, an amine-reactive and sulfhydryl-reactive crosslinker (e.g. N-succin-imidyl 3-(2-pyridyldithio)propionate, a carbonyl-reactive and sulfhydryl-reactive crosslinker (e.g. 4-(4-N-maleimi-dophenyl)butyric acid hydrazide), or a combination thereof.

In some embodiments, the cross-linking agent is a tri-functional cross-linkers, such as, for example, 4-azido-2-nitrophenylbiocytin-4-nitrophenyl ester, sulfosuccinimidyl-2-[6-biotinamido]-2-(p-azidobenzamido)hexanoamido] ethyl-1,3'-dithiopropionate (sulfo-SBED), or a combination thereof.

In another embodiment, the cross-linking agent is an enzyme, which in one embodiment, is a transglutaminase, peroxidase, xanthine oxidase, polymerase, ligase, or a combination thereof.

The choice of concentration of the cross-linking agent utilized for activity will vary, as a function of the volume, agent and polymer chosen, in a given application, as will be appreciated by one skilled in the art.

In one embodiment, the aragonite or calcite is associated with the gel via physical association, such as, for example, via imbibing of any means, for example via the application of heat to promote the physical association. In another embodiment, the aragonite- or calcite-associated gel may be attached via physical association, such as, for example, via imbibing of any means, for example via air drying of the gel or via the application of heat thereto, to promote the physical association, or via the use of a cross-linking agent as described herein.

Effector Compounds

In one embodiment, the biomatrices further comprise an effector compound, or compound of interest. In one embodiment the effector compound is applied directly to the gels of the biomatrices of this invention, or are a component of the kits of this invention for incorporation into the biomatrices as herein described. In one embodiment, the effector compound, or compound of interest is applied directly, without being dispersed in any solvent.

In another embodiment, the effector compound is an antibiotic, an antiviral, an antifungal, an anti-helminth, an anti-inflammatory, an antihistamine, an immunomodulatory, an anticoagulant, a surfactant, a bronchodilator, an antibody, a beta-adrenergic receptor inhibitor, a calcium channel blocker, an ace inhibitor, a growth factor, a hormone, a DNA, an siRNA, a vector or any combination thereof.

In one embodiment, the term "effector compound" refers to any agent or compound, which has a specific purpose or application which is useful in the treatment, prevention, inhibition, suppression, delay or reduction of incidence of infection, a disease, a disorder, or a condition, when applied to the biomatrices, kits and/or methods of this invention. An effector compound of this invention, in one embodiment, will produce a desired effect which is exclusive to the ability to image the compound. In some embodiments, the effector compound may be useful in imaging a site at which the compound is present, however, such ability is secondary to the purpose or choice of use of the compound.

In one embodiment, the term "compound of interest", as used anywhere herein, refers to any desired molecule, and may comprise, inter alia, a nucleic acid, a hormone, a growth factor, a cytokine, a chemokine, a bone morphogenetic protein, a matrix metallo-proteinases, a peptide, a drug, an enzyme, a label or a combination thereof.

The term "effector compound" is to be understood to include the terms "drug" and "agent", as well, when referred to herein, and represent a molecule whose incorporation within the biomatrices and/or kits of this invention, or whose use thereof, is desired. In one embodiment, the agent is incorporated directly within the biomatrices, and/or kits of this invention or, in another embodiment, the agent is incorporated within the biomatrices and/or kits of this invention, either by physical interaction with the gels, foams, films, particles, compositions, and/or kits of this invention, or association thereto.

In one embodiment, compounds for use in biomatrices and/or kits of this invention and/or methods of this invention may comprise, inter-alia, an antibody or antibody fragment, a peptide, an oligonucleotide, a ligand for a biological target, an immunoconjugate, a chemomimetic functional group, a glycolipid, a labelling agent, an enzyme, a metal ion chelate, an enzyme cofactor, a cytotoxic compound, a bactericidal compound, a bacteriostatic compound, a fungicidal compound, a fungistatic compound, a chemotherapeutic, a growth factor, a hormone, a cytokine, a toxin, a prodrug, an antimetabolite, a microtubule inhibitor, a radioactive material, a targeting moiety, or any combination thereof.

In one embodiment, the term "antibody or antibody fragment" refers to intact antibody molecules as well as functional fragments thereof, such as Fab, F(ab')2, and Fv that are capable of binding to an epitope. In one embodiment, an Fab fragment refers to the fragment which contains a monovalent antigen-binding fragment of an antibody molecule, which can be produced by digestion of whole antibody with the enzyme papain to yield an intact light chain and a portion of one heavy chain. In one embodiment, Fab' fragment refers to a part of an antibody molecule that can be obtained by treating whole antibody with pepsin, followed by reduction, to yield an intact light chain and a portion of the heavy chain. Two Fab' fragments may be obtained per antibody molecule. In one embodiment, (Fab')2 refers to a fragment of an antibody that can be obtained by treating whole antibody with the enzyme pepsin without subsequent reduction. In another embodiment, F(ab')2 is a dimer of two Fab' fragments held together by two disulfide bonds. In one embodiment, Fv, may refer to a genetically engineered fragment containing the variable region of the light chain and the variable region of the heavy chain expressed as two chains. In one embodiment, the antibody fragment may be a single chain antibody ("SCA"), a genetically engineered molecule containing the variable region of the light chain and the variable region of the heavy chain, linked by a suitable polypeptide linker as a genetically fused single chain molecule.

Methods of making these fragments are known in the art. (See for example, Harlow and Lane, Antibodies: A Laboratory Manual, Cold Spring Harbor Laboratory, New York, 1988, incorporated herein by reference).

In one embodiment, compounds for use in the biomatrices and/or kits of this invention and/or methods of this invention may comprise, inter-alia, a peptide. In some embodiments, the term "peptide" refers to native peptides (either degradation products, synthetically synthesized peptides or recombinant peptides) and/or peptidomimetics (typically, synthetically synthesized peptides), such as peptoids and semipeptoids which are peptide analogs, which may have, for example, modifications rendering the peptides more stable while in a body or more capable of penetrating into cells. Such modifications include, but are not limited to N terminus modification, C terminus modification, peptide bond modification, including, but not limited to, CH2-NH, CH2-S, CH2-S=O, O=C—NH, CH2-O, CH2-CH2, S=C—NH, CH=CH or CF=CH, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein.

In one embodiment, the term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" may include both D- and L-amino acids.

In one embodiment, the biomatrices and/or kits of this invention and/or methods of this invention comprise or make use of an oligonucleotide, a nucleic acid, or a vector. In some embodiments, the term "oligonucleotide" is interchangeable with the term "nucleic acid", and may refer to a molecule, which may include, but is not limited to, prokaryotic sequences, eukaryotic mRNA, cDNA from eukaryotic mRNA, genomic DNA sequences from eukaryotic (e.g., mammalian) DNA, and even synthetic DNA sequences. The term also refers to sequences that include any of the known base analogs of DNA and RNA.

The biomatrices and/or kits of this invention and/or methods of this invention may comprise nucleic acids, in one embodiment, or in another embodiment, the biomatrices and/or kits of this invention and/or methods of this invention may include delivery of the same, as a part of a particular vector. In one embodiment, polynucleotide segments encoding sequences of interest can be ligated into commercially available expression vector systems suitable for transducing/transforming mammalian cells and for directing the expression of recombinant products within the transduced cells. It will be appreciated that such commercially available vector systems can easily be modified via commonly used recombinant techniques in order to replace, duplicate or mutate existing promoter or enhancer sequences and/or introduce any additional polynucleotide sequences such as for example, sequences encoding additional selection markers or sequences encoding reporter polypeptides.

The efficacy of a particular expression vector system and method of introducing nucleic acid into a cell can be assessed by standard approaches routinely used in the art. For example, DNA introduced into a cell can be detected by a filter hybridization technique (e.g., Southern blotting) and RNA produced by transcription of introduced DNA can be detected, for example, by Northern blotting, RNase protection or reverse transcriptase-polymerase chain reaction (RT-PCR). The gene product can be detected by an appropriate assay, for example by immunological detection of a produced protein, such as with a specific antibody, or by a functional assay to detect a functional activity of the gene product, such as an enzymatic assay. If the gene product of interest to be expressed by a cell is not readily assayable, an expression system can first be optimized using a reporter gene linked to the regulatory elements and vector to be used. The reporter gene encodes a gene product, which is easily detectable and, thus, can be used to evaluate efficacy of the system. Standard reporter genes used in the art include genes encoding β-galactosidase, chloramphenicol acetyl transferase, luciferase and human growth hormone.

As will be appreciated by one skilled in the art, a fragment or derivative of a nucleic acid sequence or gene that encodes for a protein or peptide can still function in the same manner as the entire, wild type gene or sequence. Likewise, forms of nucleic acid sequences can have variations as compared to wild type sequences, nevertheless encoding the protein or peptide of interest, or fragments thereof, retaining wild type function exhibiting the same biological effect, despite these variations. Each of these represents a separate embodiment of this present invention.

The nucleic acids can be produced by any synthetic or recombinant process such as is well known in the art. Nucleic acids can further be modified to alter biophysical or biological properties by means of techniques known in the art. For example, the nucleic acid can be modified to increase its stability against nucleases (e.g., "end-capping"), or to modify its solubility, or binding affinity to complementary sequences.

Methods for modifying nucleic acids to achieve specific purposes are disclosed in the art, for example, in Sambrook et al. (1989). Moreover, the nucleic acid sequences of the invention can include one or more portions of nucleotide sequence that are non-coding for the protein of interest. Variations in the DNA sequences, which are caused by point mutations or by induced modifications (including insertion, deletion, and substitution) to enhance the activity, half-life or production of the polypeptides encoded thereby, are also encompassed in the invention.

In one embodiment, the agent is one which may inhibit gene expression in a subject. In one embodiment, the agent that inhibits gene expression, activity or function comprises a nucleic acid. The nucleic acid may, in one embodiment, be DNA, or in another embodiment, the nucleic acid is RNA. In other embodiments, the nucleic acid may be single or double stranded.

In one embodiment, the agents used in the biomatrices and/or kits of this invention and/or methods of this invention may be used for gene silencing applications. In one embodiment, the activity or function of a particular gene is suppressed or diminished, via the use of antisense oligonucleotides. In one embodiment, the antisense molecules may be conjugated to the polymers of this invention. Inhibition of gene expression, activity or function is effected, in another embodiment, via the use of small interfering RNAs, which provides sequence-specific inhibition of gene expression for example, as described in Elbashir S M, et al (2001) Nature 411:494-498; Fire et al. (1998) Nature 391: 806-11; Waterhouse, P. M., et al. (1998). Proc. Natl. Acad. Sci. USA 95, 13959-13964 and Wang, Z., et al. (2000). J. Biol. Chem. 275, 40174-40179.

In some embodiments, transfected, transduced or transformed cells, may be incorporated into gels or compositions or materials of this invention, so that engineered cells may comprise the gels or compositions or materials of this invention.

In one embodiment, the nucleic acid encodes for an antibacterial, antiviral, antifungal or antiparasitic peptide or protein. In another embodiment, the nucleic acid encodes for a peptide or protein with cytotoxic or anti-cancer activity. In another embodiment, the nucleic acid encodes for an enzyme, a receptor, a channel protein, a hormone, a cytokine, a bone morphogenetic protein, a matrix metalloproteinase, or a growth factor. In another embodiment, the nucleic acid encodes for a peptide or protein, which is immunostimulatory. In another embodiment, the nucleic acid encodes for a peptide or protein, which inhibits inflammatory or immune responses.

In one embodiment, biomatrices and/or kits of this invention and/or methods of this invention may further comprise or make use of a "drug" or "compound" or "agent", which refers in some embodiments, to a substance applicable for use in the diagnosis, or in another embodiment, cure, or in another embodiment, mitigation, or in another embodiment, treatment, or in another embodiment, prevention, or in another embodiment, suppression, or in another embodiment, delay in progression, or in another embodiment delay or prevention of relapse, or in another embodiment, reduction in incidence of a disease, disorder, condition or infection. In one embodiment, the "drug" or "compound" or "agent" for use in the biomatrices and/or kits of this invention and/or methods of this invention this invention, refers to any substance which affects the structure or function of the target to which it is applied.

In another embodiment, the "drug" or "compound" or "agent" for use in the gels biomatrices and/or kits of this invention and/or methods of this invention, is a molecule that alleviates a symptom of a disease or disorder when administered to a subject afflicted thereof. In one embodiment, the "drug" or "compound" or "agent" for use in biomatrices and/or kits of this invention and/or methods of this invention, is a synthetic molecule, or in another embodiment, a naturally occurring compound isolated from a source found in nature.

In one embodiment, the "drug" or "compound" or "agent" for use in the biomatrices and/or kits of this invention and/or methods of this invention, may comprise antihypertensives, antidepressants, antianxiety agents, anticlotting agents, anticonvulsants, blood glucose-lowering agents, decongestants, antihistamines, histamine, antitussives, anti-inflammatories, antipsychotic agents, cognitive enhancers, cholesterol-reducing agents, antiobesity agents, autoimmune disorder agents, anti-impotence agents, antibacterial and antifungal agents, hypnotic agents, anti-Parkinsonism agents, antibiotics, antiviral agents, anti-neoplastics, barbituates, sedatives, nutritional agents, beta blockers, emetics, anti-emetics, diuretics, anticoagulants, cardiotonics, androgens, corticoids, anabolic agents, growth hormone secretagogues, anti-infective agents, coronary vasodilators, carbonic anhydrase inhibitors, antiprotozoals, gastrointestinal agents, serotonin antagonists, anesthetics, hypoglycemic agents, dopaminergic agents, anti-Alzheimer's Disease agents, antiulcer agents, platelet inhibitors and glycogen phosphorylase inhibitors, insulin, diagnostic markers, drugs used for the control of birth, natural products, calcyfying agents, cell mediators, cell inhibitors, antimitotic agents, alkylating agents, immunomodulators, analgesics, vaccines, sympathomimetic agents, cholinomimetic agents, adrenergic and adrenergic neuron blocking agent, antimuscarinic and antispasmodic agents, skeletal muscle relaxant, anti-migraine agents, central nervous system stimulants, immunosuppressive agents, vitamins, parasiticides, drugs for the treatment of ipo-/iper-tyroidism, osteoporosis, osteopetrosis, arthritis, epilepsy, glaucoma and eye diseases.

In one embodiment, examples of the "drug" or "compound" or "agent" for use in the biomatrices and/or kits of this invention and/or methods of this invention comprise, inter-alia, antihypertensives including prazosin, nifedipine, trimazosin, amlodipine, and doxazosin mesylate; the antianxiety agent hydroxyzine; a blood glucose lowering agent such as glipizide; an anti-impotence agent such as sildenafil citrate; anti-neoplastics such as chlorambucil, lomustine or echinomycin; anti-inflammatory agents such as betamethasone, prednisolone, piroxicam, aspirin, flurbiprofen and (+)-N-{4-[3-(4-fluorophenoxy)phenoxy]-2-cyclopenten-1-yl}-N-hyroxyurea; antivirals such as acyclovir, nelfinavir, or virazole; vitamins/nutritional agents such as retinol and vitamin E; emetics such as apomorphine; diuretics such as chlorthalidone and spironolactone; an anticoagulant such as dicumarol; cardiotonics such as digoxin and digitoxin; androgens such as 17-methyltestosterone and testosterone; a mineral corticoid such as desoxycorticosterone; a steroidal hypnotic/anesthetic such as alfaxalone; an anabolic agent such as fluoxymesterone or methanstenolone; antidepression agents such as fluoxetine, pyroxidine, venlafaxine, sertraline, paroxetine, sulpiride, [3,6-dimethyl-2-(2,4,6-trimethylphenoxy)-pyridin-4-yl]-(lethylpropyl)-amine or 3,5-dimethyl-4-(3'-pentoxy)-2-(2',4',6'-trimethylphenoxy)pyridine; an antibiotic such as ampicillin and penicillin G or belonging to the family of penicillines, cephalosporins, aminoglycosidics, macrolides, carbapenem and penem, beta-lactam monocyclic, inhibitors of beta-lactamases, tetracyclins, polipeptidic antibiotics, chloramphenicol and derivatives, fusidic acid, lincomicyn, novobiocine, spectinomycin, polyetheric ionophores, quinolones; an anti-infective such as benzalkonium chloride or chlorhexidine; a coronary vasodilator such as nitroglycerin or mioflazine; a hypnotic such as etomidate; a carbonic anhydrase inhibitor such as acetazolamide or chlorzolamide; an antifungal such as econazole, terconazole, fluconazole, voriconazole or griseofulvin; an antiprotozoal such as metronidazole; an imidazole-type antineoplastic such as tubulazole; an anthelmintic agent such as thiabendazole or oxfendazole; an antihistamine such as astemizole, levocabastine, cetirizine, or cinnarizine; a decongestant such as pseudoephedrine; antipsychotics such as fluspirilene, penfluridole, risperidone or ziprasidone; a gastrointestinal agent such as loperamide or cisapride; a serotonin antagonist such as ketanserin or mianserin; an anesthetic such as lidocaine; a hypoglycemic agent such as acetohexamide; an anti-emetic such as dimenhydrinate; an antibacterial such as cotrimoxazole; a dopaminergic agent such as L-DOPA; anti-Alzheimer agents such as THA or donepezil; an anti-ulcer agent/H2 antagonist such as famotidine; a sedative/hypnotic such as chlordiazepoxide or triazolam; a vasodilator such as alprostadil; a platelet inhibitor such as prostacyclin; an ACE inhibitor/antihypertensive such as enalaprilic acid or lisinopril; a tetracycline antibiotic such as oxytetracycline or minocycline; a macrolide antibiotic such as azithromycin, clarithromycin, erythromycin or spiramycin; and glycogen phosphorylase inhibitors such as [R—(R*S*)]-5-chloro-N-[2-hydroxy-3 {methoxymethylamino}-3-oxo-1-(phenylmethyl)-propyl]-IH-indole-2-carboxamide or 5-chloro-1-Hindole-2-carboxylic acid [(IS)-benzyl(2R)-hydroxy-3-((3R,4S)dihydroxy-pyrrolidin-1-yl-)-oxypropyl]amide.

Further examples of the "drug" or "compound" or "agent" for use in the biomatrices and/or kits of this invention and/or methods of this invention, are the glucose-lowering drug chlorpropamide, the anti-fungal fluconazole, the anti-hypercholesterolemic atorvastatin calcium, the antipsychotic thiothixene hydrochloride, the anxiolytics hydroxyzine hydrochloride or doxepin hydrochloride, the anti-hypertensive amlodipine besylate, the antiinflammatories piroxicam and celicoxib and valdicoxib, and the antibiotics carbenicillin indanyl sodium, bacampicillin hydrochloride, troleandomycin, and doxycycline hyclate.

In another embodiment a "drug" or "compound" or "agent" for use in biomatrices and/or kits of this invention and/or methods of this invention, may comprise other antineoplastic agents such as platinum compounds (e.g., spiroplatin, cisplatin, and carboplatin), methotrexate, fluorouracil, adriamycin, mitomycin, ansamitocin, bleomycin, cytosine arabinoside, arabinosyl adenine, mercaptopolylysine, vincristine, busulfan, chlorambucil, melphalan (e.g., PAM, L-PAM or phenylalanine mustard), mercaptopurine, mitotane, procarbazine hydrochloride dactinomycin (actinomycin D), daunorubicin hydrochloride, doxorubicin hydrochloride, paclitaxel and other taxenes, rapamycin, manumycin A, TNP-470, plicamycin (mithramycin), aminoglutethimide, estramustine phosphate sodium, flutamide, leuprolide acetate, megestrol acetate, tamoxifen citrate, testolactone, trilostane, amsacrine (m-AMSA), asparaginase (L-asparaginase) Erwina asparaginase, interferon .alpha.-2a, interferon .alpha.-2b, teniposide (VM-26), vinblastine sulfate (VLB), vincristine sulfate, bleomycin sulfate, hydroxyurea, procarbazine, and dacarbazine; mitotic inhibitors such as etoposide, colchicine, and the vinca alkaloids, radiopharmaceuticals such as radioactive iodine and phosphorus products; hormones such as progestins, estrogens and antiestrogens; anti-helmintics, antimalarials, and anti-tuberculosis drugs; biologicals such as immune serums, antitoxins and antivenoms; rabies prophylaxis products; bacterial vaccines; viral vaccines; respiratory products such as xanthine derivatives theophylline and aminophylline; thyroid agents such as iodine products and anti-thyroid agents; cardiovascular products including chelating agents and mercurial diuretics and cardiac glycosides; glucagon; blood products such as parenteral iron, hemin, hematoporphyrins and their derivatives; biological response modifiers such as muramyldipeptide, muramyltripeptide, microbial cell wall components, lymphokines (e.g., bacterial endotoxin such as lipopolysaccharide, macrophage activation factor), sub-units of bacteria (such as Mycobacteria, Corynebacteria), the synthetic dipeptide N-acetyl-muramyl-L-ala-nyl-D-isoglutamine; anti-fungal agents such as ketoconazole, nystatin, griseofulvin, flucytosine (5-fc), miconazole, Amphotericin B, ricin, cyclosporins, and β-lactam antibiotics (e.g., sulfazecin); hormones such as growth hormone, melanocyte stimulating hormone, estradiol, beclomethasone dipropionate, betamethasone, betamethasone acetate and betamethasone sodium phosphate, vetamethasone disodium phosphate, vetamethasone sodium phosphate, cortisone acetate, dexamethasone, dexamethasone acetate, dexamethasone sodium phosphate, flunisolide, hydrocortisone, hydrocortisone acetate, hydrocortisone cypionate, hydrocortisone sodium phosphate, hydrocortisone sodium succinate, methylprednisolone, methylprednisolone acetate, methylprednisolone sodium succinate, paramethasone acetate, prednisolone, prednisolone acetate, prednisolone sodium phosphate, prednisolone tebutate, prednisone, triamcinolone, triamcinolone acetonide, triamcinolone diacetate, triamcinolone hexacetonide, fludrocortisone acetate, oxytocin, vassopressin, and their derivatives; vitamins such as cyanocobalamin neinoic acid, retinoids and derivatives such as retinol palmitate, and .alpha.-tocopherol; peptides, such as manganese super oxide dismutase; enzymes such as alkaline phosphatase; anti-allergic agents such as amelexanox; anticoagulation agents such as phenprocoumon and heparin; circulatory drugs such as propranolol; metabolic potentiators such as glutathione; antituberculars such as para-aminosalicylic acid, isoniazid, capreomycin sulfate cycloserine, ethambutol hydrochloride ethionamide, pyrazinamide, rifampin, and streptomycin sulfate; antivirals such as amantadine azidothymidine (AZT, DDI, Foscarnet, or Zidovudine), ribavirin and vidarabine monohydrate (adenine arabinoside, ara-A); antianginals such as diltiazem, nifedipine, verapamil, erythritol tetranitrate, isosorbide dinitrate, nitroglycerin (glyceryl trinitrate) and pentaerythritol tetranitrate; anticoagulants such as phenprocoumon, heparin; antibiotics such as dapsone, chloramphenicol, neomycin, cefaclor, cefadroxil, cephalexin, cephradine erythromycin, clindamycin, lincomycin, amoxicillin, ampicillin, bacampicillin, carbenicillin, dicloxacillin, cyclacillin, picloxacillin, hetacillin, methicillin, nafcillin, oxacillin, penicillin including penicillin G and penicillin V, ticarcillin rifampin and tetracycline; antiinflammatories such as diflunisal, ibuprofen, indomethacin, meclofenamate, mefenamic acid, naproxen, oxyphenbutazone, phenylbutazone, piroxicam, sulindac, tolmetin, aspirin and salicylates; antiprotozoans such as chloroquine, hydroxychloroquine, metronidazole, quinine and meglumine antimonate; antirheumatics such as penicillamine; narcotics such as paregoric; opiates such as codeine, heroin, methadone, morphine and opium; cardiac glycosides such as deslanoside, digitoxin, digoxin, digitalin and digitalis; neuromuscular blockers such as atracurium mesylate, gallamine triethiodide, hexafluorenium bromide, metocurine iodide, pancuronium bromide, succinylcholine chloride (suxamethonium chloride), tubocurarine chloride and vecuronium bromide; sedatives (hypnotics) such as amobarbital, amobarbital sodium, aprobarbital, butabarbital sodium, chloral hydrate, ethchlorvynol, ethinamate, flurazepam hydrochloride, glutethimide, methotrimeprazine hydrochloride, methyprylon, midazolam hydrochloride, paraldehyde, pentobarbital, pentobarbital sodium, phenobarbital sodium, secobarbital sodium, talbutal, temazepam and triazolam; local anesthetics such as bupivacaine hydrochloride, chloroprocaine hydrochloride, etidocaine hydrochloride, lidocaine hydrochloride, mepivacaine hydrochloride, procaine hydrochloride and tetracaine hydrochloride; general anesthetics such as droperidol, etomidate, fentanyl citrate with droperidol, ketamine hydrochloride, methohexital sodium and thiopental sodium; and radioactive particles or ions such as strontium, iodide rhenium and yttrium.

In one embodiment, the "drug" or "compound" or "agent" for use in the biomatrices and/or kits of this invention and/or methods of this invention is a therapeutic compound. In one embodiment, the therapeutic compound is a peptide, a protein or a nucleic acid. In another embodiment, the therapeutic compound is an antibacterial, antiviral, antifungal or antiparasitic compound. In another embodiment, the therapeutic compound has cytotoxic or anti-cancer activity. In another embodiment, the therapeutic compound is an enzyme, a receptor, a channel protein, a hormone, a cytokine or a growth factor. In another embodiment, the therapeutic compound is immunostimulatory. In another embodiment, the therapeutic compound inhibits inflammatory or immune responses.

In one embodiment, the term "therapeutic", refers to a molecule, which when provided to a subject in need, provides a beneficial effect. In some cases, the molecule is therapeutic in that it functions to replace an absence or diminished presence of such a molecule in a subject. In one embodiment, the molecule is a nucleic acid coding for the expression of a protein is absent, such as in cases of an endogenous null mutant being compensated for by expression of the foreign protein. In other embodiments, the endogenous protein is mutated, and produces a non-functional protein, compensated for by the expression of a heterologous functional protein. In other embodiments, expression of a heterologous protein is additive to low endogenous levels, resulting in cumulative enhanced expression of a given protein. In other embodiments, the molecule stimulates a signaling cascade that provides for expression, or secretion, or others of a critical element for cellular or host functioning.

In another embodiment, the therapeutic molecule may be natural or non-natural insulins, amylases, proteases, lipases, kinases, phosphatases, glycosyl transferases, trypsinogen, chymotrypsinogen, carboxypeptidases, hormones, ribonucleases, deoxyribonucleases, triacylglycerol lipase, phospholipase A2, elastases, amylases, blood clotting factors, UDP glucuronyl transferases, ornithine transcarbamoylases, cytochrome p450 enzymes, adenosine deaminases, serum thymic factors, thymic humoral factors, thymopoietins, growth hormones, somatomedins, costimulatory factors, antibodies, colony stimulating factors, erythropoietin, epidermal growth factors, hepatic erythropoietic factors (hepatopoietin), liver-cell growth factors, interleukins, interferons, negative growth factors, fibroblast growth factors, transforming growth factors of the α family, transforming growth factors of the β family, gastrins, secretins, cholecystokinins, somatostatins, serotonins, substance P, transcription factors or combinations thereof.

In another embodiment, this invention also comprises incorporation of any toxic substance for therapeutic purpose. In one embodiment, the biomatrices and/or kits of this invention and/or methods of this invention, may incorporate an oligonucleotide encoding a suicide gene, which when in contact with diseased cells or tissue, is expressed within such cells. In one embodiment, the term "suicide gene" refers to a nucleic acid coding for a product, wherein the product causes cell death by itself or in the presence of other compounds. A representative example of a suicide gene is one, which codes for thymidine kinase of herpes simplex virus. Additional examples are thymidine kinase of varicella zoster virus and the bacterial gene cytosine deaminase, which can convert 5-fluorocytosine to the highly cytotoxic compound 5-fluorouracil.

Suicide genes may produce cytotoxicity by converting a prodrug to a product that is cytotoxic. In one embodiment, the term "prodrug" means any compound that can be converted to a toxic product for cells. Representative examples of such a prodrug is gancyclovir which is converted in vivo to a toxic compound by HSV-thymidine kinase. The gancyclovir derivative subsequently is toxic to cells. Other representative examples of prodrugs include acyclovir, FIAU [1-(2-deoxy-2-fluoro-β-D-arabinofuranosyl)-5-iodouracil], 6-methoxypurine arabinoside for VZV-TK, and 5-fluorocytosine for cytosine deaminase.

In another embodiment, the cytotoxic agent may comprise any agent that is detrimental to cells, such as, for example, taxol, cytochalasin B, gramicidin D, ethidium bromide, emetine, mitomycin, etoposide, tenoposide, vincristine, vinblastine, colchicin, doxorubicin, daunorubicin, dihydroxy anthracinedione, mitoxantrone, mithramycin, actinomycin D, 1-dehydrotestosterone, glucocorticoids, procaine, tetracaine, lidocaine, propranolol, and puromycin and analogs or homologs thereof.

In one embodiment the drug, agent or effector compound may comprise any compound of choice to suit a particular application. Such compounds may comprise, inter-alia, wound healing promotional agents, antiseptics, anti-infectives, tissue engineering compounds, recombinant products or constructs, hormones, growth factors, enzymes, cytokines, antibodies, anti-inflammatories, immune modulating compounds, immunosuppressant, antihypertensives, antidepressants, antianxiety agents, anticlotting agents, anticonvulsants, blood glucose-lowering agents, decongestants, antihistamines, antitussives, antipsychotic agents, cognitive enhancers, cholesterol-reducing agents, antiobesity agents, autoimmune disorder agents, anti-impotence agents, antibacterial and antifungal agents, hypnotic agents, anti-Parkinsonism agents, anti-neoplastics, barbituates, sedatives, nutritional agents, beta blockers, emetics, anti-emetics, diuretics, anticoagulants, cardiotonics, androgens, corticoids, anabolic agents, growth hormone secretagogues, coronary vasodilators, carbonic anhydrase inhibitors, antiprotozoals, gastrointestinal agents, serotonin antagonists, anesthetics, hypoglycemic agents, dopaminergic agents, anti-Alzheimer's disease agents, anti-ulcer agents, platelet inhibitors and glycogen phosphorylase inhibitors.

In one embodiment, the biomatrices of the present invention may be used to adsorb or bind, and deliver, other therapeutically active substances which assist in the cartilage and/or bone repair or regeneration process, or which have other desired therapeutic activity. Such substances include, by way of example, known synthetic or semisynthetic antibiotics which may be introduced into the pore cavities of the shaped product or structure, or a growth factor such as transforming growth factor or one of the bone morphogenic proteins which can be used to assist or promote bone growth.

In any of the embodiments herein, biomatrices for use in the present invention may further comprise, or be delivered with, other compounds such as, for example, antioxidants, growth factors, cytokines, antibiotics, anti-inflammatories, immunosuppressors, preservative, pain medication, other therapeutics, and excipient agents. In one embodiment, examples of growth factors that may be administered in addition to the HMG-CoA reductase inhibitor include, but are not limited to, epidermal growth factor (EGF), transforming growth factor-alpha (TGF-α), transforming growth factor-beta (TGF-β), human endothelial cell growth factor (ECGF), granulocyte macrophage colony stimulating factor (GM-CSF), bone morphogenetic protein (BMP), nerve growth factor (NGF), vascular endothelial growth factor (VEGF), fibroblast growth factor (FGF), insulin-like growth factor (IGF), cartilage derived morphogenetic protein (CDMP), platelet derived growth factor (PDGF), or any combinations thereof. Examples of antibiotics include antimicrobials and antibacterials.

In any of the embodiments herein, biomatrices for use in the present invention may further comprise, or be delivered with a chondrogenic and/or osteogenic support agent. Such "support agent" will be understood to include any protein, which participates in cartilage and/or bone formation, such as the therapeutic proteins described above, and in some embodiments, will include other components which participate in cartilage and/or bone formation, such as, for example, extracellular matrix components, such as glycosaminoglycans, collagens, chitosan, fibrin, or combinations thereof. In some embodiments, the support agent may include glycoproteins, oligosaccharides, and the like, which participate in cartilage and/or bone formation, as will be appreciated by the skilled artisan.

Stem or Progenitor or Precursor Cells

In some embodiments, the biomatrices of this invention incorporate stem or progenitor or precursor cells. Such cells can be obtained directly from a mammalian donor, e.g., a patient's own cells, from a culture of cells from a donor, or from established cell culture lines. In some embodiments, the mammal is a mouse, rat, rabbit, guinea pig, hamster, cow, pig, horse, goat, sheep, dog, cat, monkey, ape or any simian, or a human. Cells of the same species and/or of the same immunological profile can be obtained by biopsy, either from the patient or a close relative. Using standard cell culture techniques and conditions, the cells are then grown in culture until confluent and used when needed. The cells may be cultured until a sufficient number of cells have been obtained for a particular application.

In one embodiment, the coral or biomatrix is seeded with a precursor cell. In one embodiment, the precursor cell is a mesenchymal stem cell. In other embodiments, the cell may be a mesenchymal cell; chondrocyte; fibrochondrocyte; osteocyte; osteoblast; osteoclast; synoviocyte; chondroblast, bone marrow cell; stromal cell; stem cell; embryonic stem cell; precursor cell, derived from adipose tissue; peripheral blood progenitor cell; stem cell isolated from adult tissue; genetically transformed cell; or a combination thereof. In another embodiment, a precursor cell may refer to a combination of chondrocytes and other cells; a combination of osteocytes and other cells; a combination of synoviocytes and other cells; a combination of bone marrow cells and other cells; a combination of mesenchymal cells and other cells; a combination of stromal cells and other cells; a combination of stem cells and other cells; a combination of embryonic stem cells and other cells; a combination of precursor cells isolated from adult tissue and other cells; a combination of peripheral blood progenitor cells and other cells; a combination of stem cells isolated from adult tissue and other cells; and a combination of genetically transformed cells and other cells.

In one embodiment of the present invention, the precursor cells for use in the method of the present invention are prepared from an organ tissue of the recipient mammal (i.e. autologous), or a syngeneic mammal. In another embodiment, allogeneic and xenogeneic precursor cells may be utilized.

In another embodiment, the precursor cells utilized for administration are prepared from a donor who is human leukocyte antigen (HLA)-matched with the recipient, wherein in one embodiment, HLA is the major histocompatibility complex in humans. In one embodiment, donor and recipient are matched for class I major histocompatibility complex (MHC) genes, class II MHC genes, or a combination thereof. In one embodiment, class I MHC genes comprise HLA-A, HLA-B, and HLA-C, wherein in one embodiment, a mismatch of class I MHC genes increases the risk of graft rejection, and in one embodiment, class II MHC genes comprise HLA-DPA1, HLA-DPB1, HLA-DQA1, HLA-DQB1, HLA-DRA, HLA-DRB1, wherein in one embodiment, a mismatch of class II MHC genes increases the risk of GVHD. In another embodiment, donor and recipient are matched for HLA-DM and HLA-DO genes.

In some embodiments, the aragonite or calcite and/or other components of the biomatrices, or biomatrices of this invention are seeded with stem and/or precursor cells in the presence of a chelator. In one embodiment, the term chelator refers to a chelating agent or chelating reagent, which in one embodiment, comprises a calcium chelator. In one embodiment, the chelator may comprise: ethylenediamine-N,N,N',N'-tetraacetic acid (EDTA), O,O'-bis(2-aminophenylethyleneglycol)ethylenediamine-N,N,N',N'-tetraacetic acid (BAPTA), N,N-bis(2-hydroxyethyl) glycine (Bicine), trans-1,2-diaminocyclohexane-ethylenediamine-N,N,N',N'-tetraacetic acid (CyDTA), 1,3-diamino-2-hydroxypropane-ethylenediamine-N,N,N',N'-tetraacetic acid (DPTA-OH), diethylenetriamine-N,N,N',N'',N''-pentaacetic acid (DPTA), ethylenediamine-N,N'-dipropionic acid dihydrochloride (EDDP), ethylenediamine-N,N'-bis(methylenephosphonic acid) hemihydrate (EDDPO), N-(2-hydroxyethyl)ethylenediamine-N,N',N'-triacetic acid (EDTA-OH), ethylenediamine-N,N,N',N'-tetrakis (methylenephosphonic acid) (EDTPO), O,O'-bis(2-aminoethyl) ethyleneglycol tetraacetic acid (EGTA), N,N'-bis(2-hydroxybenzyl)ethylenediamine-N,N'-diacetic acid (HBED), 1,6-hexamethylenediamine-N,N,N',N'-tetraacetic acid (HDTA), N-(2-hydroxyethyl)iminodiacetic acid (HIDA), iminodiacetic acid (IDA), 1,2-diaminopropane-N,N,N',N'-tetraacetic acid (methyl-EDTA), nitrilotriacetic acid (NTA), nitrilotripropionic acid (NTP), nitrilotris(methylenephosphonic acid) trisodium salt (NTPO), N,N,N',N'-tetrakis(2-pyridylmethyl) ethylenediamine (TPEN), and triethylenetetramine-N,N,N',N'',N''-hexaacetic acid (TTHA), rhod-2, DMSA, FLUO 3, FURA 2, INDO 1, QUIN 2, or other chelators known in the art, or a combination thereof. In another embodiment, a chelator is a zinc, manganese, magnesium, copper, iron, chelator, or a combination thereof. In one embodiment, a zinc chelator comprises ethylenediiminodi-2-pentanedioic acid, Zinquin, histidine, or the chelators described hereinabove, or a combination thereof.

In one embodiment, aragonite or calcite and/or other components of the biomatrices and/or biomatrices are seeded with a precursor cell in culture in the presence of a chelator for a period of time sufficient to seed said precursory cell in said aragonite or calcite. In one embodiment, aragonite or calcite and/or other components of the biomatrices and/or biomatrices are seeded with the precursor cell in serum-free medium. In another embodiment, the seeding is performed in low serum medium. In another embodiment, seeding is performed in a medium to which serum was added. In one embodiment, such serum-supplemented medium comprises 10% serum substitute supplement, 10% Fetal bovine serum (FBS or FCS), enriched calf serum, horse serum, goat serum, human serum, or a combination thereof.

By "cell culture" or "culture" is meant the maintenance of cells in an artificial, in vitro environment. It is to be understood, however, that the term "cell culture" is a generic term and may be used to encompass the cultivation not only of individual cells, but also of tissues, organs, organ systems or whole organisms, for which the terms "tissue culture," "organ culture," "organ system culture" or "organotypic culture" may occasionally be used interchangeably with the term "cell culture."

In one embodiment, media for cultivating or growing eukaryotic and/or prokaryotic cells, tissues, organs, etc, may be used to grow precursor cells of the present invention. Such media comprise Dulbecco's Modified Eagle's Medium (DMEM), Minimal Essential Medium (MEM), Basal Medium Eagle (BME), RPMI-1640, Ham's F-10, Ham's F-12, aMinimal Essential Medium (aMEM), Glasgow's Minimal Essential Medium (G-MEM), Iscove's Modified Dulbecco's Medium (IMDM), or a combination thereof. Other media that are commercially available (e.g., from Life Technologies, Inc.; Rockville, Md.) or that are otherwise known in the art may be equivalently used in accordance with the present invention including, but not limited to, 293 SFM, CD-CHO medium, VP SFM, BGJb medium, Brinster's BMOC-3 medium, cell culture freezing medium, CMRL media, EHAA medium, eRDF medium, Fischer's medium, Gamborg's B-5 medium, GLUTAMAX™ media, Grace's insect cell media, HEPES media, Richter's modified MEM, IPL-41 insect cell media, Leibovitz's L-15 media, McCoy's 5A media, MCDB 131 medium, Media 199, Modified Eagle's Medium (MEM), Medium NCTC-109, Schneider's Drosophila medium, TC-100 insect medium, Waymouth's MB 752/1 media, William's Media E, protein free hybridoma medium II (PFHM II), AIM V media, Keratinocyte SFM, defined Keratinocyte SFM, STEMPRO® SFM, STEMPRO® complete methylcellulose medium, HepatoZYME-SFM, Neurobasal™ medium, Nerobasal-A medium, Hibernate™ A medium, Hibernate E medium, Endothelial SFM, Human Endothelial SFM, Hybridoma SFM, PFHM II, Sf 900 medium, Sf 900 II SFM, EXPRESS FIVE® medium, CHO-S-SFM, AMINOMAX-II complete medium, AMINOMAX-C100 complete medium, AMINOMAX-C100 basal medium, PB-MAX™ karyotyping medium, KARYOMAX bone marrow karyotyping medium, KNOCKOUT D-MEM and $CO_2$ independent medium.

In one embodiment, aragonite or calcite and/or other components of the biomatrices and/or biomatrices are seeded with a precursor cell in culture in the presence of a chelator for a period of time sufficient to seed the precursor cell in the coral. In one embodiment, cells are cultured for up to 72 hours. In another embodiment, cells are cultured for up to 6 hours, 12 hours, 24 hours, 36 hours, 48 hours, 4 days, 5 days, 1 week, 1.5 weeks, 2 weeks, 3 weeks, or one month. In one embodiment, precursor enrichment occurs within 1 day of seeding. In one embodiment, 50% of cells are seeded within 3 hours, 6 hours, 9 hours, 12 hours, 18 hours, 24 hours, 36 hours, 48 hours, 4 days, 5 days, or one week.

In another embodiment, the present invention provides a kit, which in one embodiment, is a kit for bone or cartilage formation, or a combination thereof, and in one embodiment, comprises aragonite or calcite, conjugated to a gel or hydrogel, or in another embodiment, the kit comprises a hydrogel comprising aragonite or calcite particles suspended therein, or in another embodiment, the kit comprises aragonite or calcite further comprising a gel or hydrogel permeating the aragonite or calcite, for example within the voids created by the porous structure of the aragonite or calcite. The kits of this invention may further comprise precursor cells and optionally a chelator. In one embodiment, the kit further comprises other agents of interest, which may be incorporated within the biomatrices as herein described. In another embodiment, the kit comprises a aragonite- or calcite-hydrogel biomatrix, bone precursor or stem cells, and optionally a calcium chelator and/or other agents of interest.

In some embodiments, the marine organism skeletal derivative is characterized by a specific fluid uptake capacity value of at least 75%, which specific fluid uptake capacity value is determined by establishing a spontaneous fluid uptake value divided by a total fluid uptake value.

According to this aspect, a specific fluid uptake capacity value may be determined by evaluating spontaneous uptake of a biologic fluid versus a total uptake capacity for a given sample and arriving at the specific fluid uptake capacity level, whereby if the value is over 75%, then such solid substrate will be used as described.

In some embodiments, the process for selection of the material for incorporation within a solid substrate of this invention comprises isolating a sample of a coralline-based solid material and establishing a specific fluid uptake capacity value of the material, which specific fluid uptake capacity value is determined as described.

In some embodiments, the biologic fluid is blood, and in some embodiments, the biologic fluid is water or saline. In some embodiments, the biologic fluid is hydrophilic.

In some embodiments, the biologic fluid is autologous with respect to a cell or tissue of a subject when said solid substrate is contacted with such cell or tissue of said subject.

It will be understood that the biologic fluid may be any fluid which is biocompatible and whose incorporation is appropriate within a solid substrate for the desired application.

In some embodiments, the process further comprises the step of contacting the material with a fluid for from 2-15 minutes to promote spontaneous fluid uptake of said fluid within said coralline-based solid material to arrive at said spontaneous fluid uptake value. In some embodiments, the process may allow for the contacting of the material with a fluid for from 0.5-15 minutes, or in some embodiments, from 0.5-5 minutes, or in some embodiments, 10-60 minutes, or in some embodiments, from 60 to 90 minutes, or in some embodiments, other intervals, to promote spontaneous fluid uptake. The skilled artisan will appreciate that the amount of time for which the fluid is applied to determine the spontaneous uptake may be extended or shortened as a function of the dimensions and geometry of the sample substrate being assessed. In some embodiments, when a larger sample is being assessed, the process further comprises the step of contacting the material with a fluid for from 0.1-30 seconds, 0.1-1 minutes, or 2-24 hours to promote spontaneous fluid uptake of said fluid within said coralline-based solid material to arrive at said spontaneous fluid uptake value In some embodiments, the process further comprises the step of contacting said marine organism skeletal derivative-based solid material with a fluid and applying negative pressure to said coralline-based solid material to promote maximal uptake of said fluid within said coralline-based solid material to arrive at said total fluid uptake value. In some embodiments, application of positive pressure is via the application of a vacuum to the substrate immersed in the fluid, promoting entry of the fluid therewithin.

In some embodiments, the process may further comprise the step of contacting said coralline-based material with a fluid and applying positive pressure to said coralline-based material to promote maximal uptake of said fluid within said coralline-based material to arrive at said total fluid uptake value. According to this aspect, and in some embodiments, care will be taken to ensure that the application of pressure does not in any way compromise the structural integrity of the coral.

In some embodiments, application of positive pressure is via any manual means, for example, via the use of any applicator, syringe, etc., gravitational pressure, and others, as will be appreciated by the skilled artisan. In some embodiments, application of positive pressure is via forced osmosis, centrifugation and others. In some embodiments, combinations of the described methods and others are envisioned.

In some embodiments, the marine organism skeletal derivative is characterized by having a contact angle value of less than 70 degrees when in contact with a fluid.

In some embodiments, the solid substrates characterized by a contact angle value of less than 70 degrees is comparable to samples having a specific fluid uptake capacity value of at least 75%.

In some embodiments, reference to such contact angle value is correlated with a phenomenon of enhanced attraction to and uptake of the indicated fluid within the derivative. According to this aspect, and in some embodiments, as is evident for example, when comparing FIG. 4A versus FIG. 4B, a fluid front accompanied by rapid uptake is readily seen in the marine organism skeletal derivatives described by the stated spontaneous uptake and contact value, whereas samples which do not satisfy these criteria are characterized by a lack of appreciable association and almost repulsion of the applied fluid.

In some embodiments, the marine organism skeletal derivative is characterized by having a substantial surface roughness (Ra) as measured by scanning electron microscopy or atomic force microscopy.

Methods for determining a contact angle and surface roughness are well known, and any appropriate method can be used.

Such coralline samples may be converted to hydroxyapatite prior to or following such assessment of specific fluid uptake value or contact value, as described.

According to this aspect, and in one embodiment, some or all of the coral material as herein defined, such as, for example, coral samples or nacre or others as herein described are assessed by selecting a small dry sample for use in the processes as herein described, whose region of isolation from a larger block may be ascertained, in order to provide information regarding the characteristics of the area in the block from which additional samples may be isolated and then used.

In some aspects, the sample is dried under vacuum and/or heated or pressurized or steam treated.

In some embodiments, for aspects relating to a specific fluid uptake capacity value, such value is a function of change in weight in said coralline-based solid material.

According to this aspect and in some embodiments, the dry weight for each sample is recorded and fluid as described herein is added an assay container.

According to this aspect and in some embodiments, at least 1:1 ratio of the size of the sample in mm to the volume of fluid added in ml is applied to the container. In some embodiments, the amount of fluid applied is in excess, as compared to the sample size.

According to this aspect and in some embodiments, once the initial fluid uptake is assessed, according to this aspect and in some embodiments, the solid substrate sample is then brought into contact with the fluid and the weight of the solid substrate sample is assessed. In other embodiments the specific gravity is assessed by gradient centrifugation of by the Archimedean principle.

According to this aspect and in some embodiments, spontaneous fluid uptake is assessed and a spontaneous fluid uptake value is established, based on the change in weight of the sample.

According to this aspect and in some embodiments, the specific fluid uptake capacity value is a function of change in fluid volume of applied fluid to said marine organism skeletal derivative-based solid material. According to this aspect, spontaneous fluid uptake is assessed and a spontaneous fluid uptake value is established based on the complete uptake of the volume applied to the sample.

According to this aspect and in some embodiments, the process then further comprises contacting a significantly increased amount of fluid with the sample and applying pressure thereto to promote maximal fluid uptake to the total fluid uptake capacity of the sample.

According to this aspect and in some embodiments, as noted, such pressure may be either positive or negative pressure, and the application time is for a period of time sufficient to ensure maximal uptake of the applied fluid into the marine organism skeletal derivative sample.

According to this aspect and in some embodiments, such time may include an interval of from 0.5-60 minutes, or in some embodiments, when a larger sample is being assessed, such time may include an interval of from 2-24 hours to arrive at said spontaneous fluid uptake value. It will be appreciated that the time intervals recited herein are applicable for any embodiment with regard thereto as described herein. The skilled artisan will appreciate that the amount of time for which the fluid is applied to determine the full capacity fluid uptake may be extended or shortened as a function of the dimensions and geometry of the sample substrate being assessed.

According to these aspects, the total fluid uptake capacity is thus assessed and the specific fluid uptake capacity value is then determined.

In some embodiments, the invention specifically contemplates solid substrates having a specific fluid uptake capacity value exceeding the cutoff value of 75%, for the sample to be noted optimized as a solid substrate for promoting cell or tissue growth. It will be appreciated that the invention contemplates the stated cutoff value for promoting a reasonable value that reduces the presence of appreciable false positives, i.e. solid substrates that are not as optimal for the stated applications.

In some embodiments, the invention specifically contemplates solid substrates characterized by one or more phases therein comprising a marine organism skeletal derivative having a contact angle value of less than 70 degrees, when in contact with a fluid. It will be appreciated that the invention contemplates the stated cutoff value for promoting a reasonable value that reduces the presence of appreciable false positives, i.e. solid substrates that are not as optimal for the stated applications.

In some embodiments, when the sample is utilized in vivo in subsequent applications, in some aspects, the sample is first contacted with autologous biological fluids or materials from the host prior to implantation into the same, verifying the observed enhanced fluid uptake phenotype as herein described.

In other embodiments the hydrogels of this invention may comprise a mixture of several marine originated materials or a mixture of bone and coral granules or cartilage and coral granules. In some embodiments, the hydrogel may be conjugated to a composite material comprised of multiple samples of the marine organism skeletal derivatives as herein described.

Any of the biomatrices described herein may be provided in a kit, and the same are contemplated embodiments of the invention.

The kits will thus comprise, optionally a suitable container means for the marine organism skeletal derivative/aragonite/calcite particles, the-hydrogel biomatrix, optionally precursor cells, optionally chelators, optionally crosslinking agents, optionally an applicator such as syringe, and optionally a mixing and measuring element and optionally other agents or elements of interest or a combination thereof, and optionally any additional agents that can be used in accordance with the present invention, as herein described.

For example, and in some embodiments, such kits may comprise the marine organism skeletal derivative/aragonite/calcite particles, in various sizes, which in some embodiments, may be chosen based on a desired application protocol.

In some embodiments, such kits may comprise hydrogel biomatrices, or components for assembling/reconstituting the same, and the skilled artisan will appreciate that the kits may comprise one or more components to create a varied number of matrices, which vary, in some embodiments, in terms of their composition of elements, percent inclusion of each element, viscosity, percent crosslinking, or a combination thereof.

In some embodiments, such kits may comprise additional therapeutic agents or drugs as herein described, whose incorporation is desired.

In one embodiment, a separate container is required for each substance, and/or a container for sub-components such as aragonite-calcite particles immersed in gel, and/or a container for a single agent such as container for the setting/cross linking agent. In one embodiment, any container of the kit may additionally comprise a preservative, which, in one embodiment, may increase the "shelf life" of the kit component or components to which it is added. In one embodiment all or subparts of the kit are pre-assembled and in other embodiment all parts of the kit are assembled in-situ.

The kits may comprise suitably aliquoted components of the biomatrices of the present invention. The components of the kits may be packaged either in aqueous media or in lyophilized form. The container means of the kits will generally include at least one vial, test tube, flask, bottle, syringe or other container means, into which a component may be placed, and suitably aliquoted. Where there is more than one component in the kit, the kit also will generally contain a second, third or other additional container into which the additional components may be separately placed. However, various combinations of components may be comprised in a vial.

The kits of the present invention also will typically include a means for containing reagent containers in close confinement for commercial sale. Such containers may include injection or blow-molded plastic containers into which the desired vials are retained.

In some embodiments, the kits may further comprise reagents for the assessment of the specific fluid uptake capacity value of the marine organism skeletal derivative biomatrix incorporated in the hydrogels of this invention. In some embodiments, the kits may further comprise reagents for the assessment of the contact angle value of the marine organism skeletal derivative biomatrix incorporated in the hydrogels of this invention.

When the components of the kit are provided in one and/or more liquid solutions, the liquid solution is an aqueous solution, which in one embodiment is a sterile aqueous solution. However, the components of the kit may be provided as dried powder(s). When reagents and/or components are provided as a dry powder, the powder can be reconstituted by the addition of a suitable solvent. In one embodiment, the solvent may also be provided in another container means.

Some Uses of the Biomatrices of this Invention

In one embodiment, the present invention provides a method of tissue engineering, tissue regeneration or tissue repair in a subject comprising administering to said subject a hydrogel comprising aragonite or calcite biomatrix, wherein said biomatrix is optionally seeded with a precursor cell, which can participate in said tissue engineering, tissue regeneration or tissue repair.

In another embodiment, the present invention provides a method of tissue engineering, tissue regeneration or tissue repair in a subject comprising administering to said subject a biomatrix comprising a hydrogel conjugated to aragonite or calcite, wherein said biomatrix is seeded with a precursor cell, which can participate in said tissue engineering, tissue regeneration or tissue repair.

According to these aspects of the invention, and in one embodiment, the biomatrix may comprise any embodiment as herein described.

In some embodiments, the tissue whose engineering, regeneration or repair is desired is bone, thus this invention provides a method of inducing or enhancing bone formation in a subject comprising administering to said subject a biomatrix comprising a hydrogel conjugated to a coral, wherein said biomatrix is optionally seeded with a precursor cell, which can participate in said bone engineering, bone regeneration or bone repair, or in another embodiment administering to the subject a hydrogel comprising coral biomatrix, wherein said biomatrix is seeded with a precursor cell, which can participate in said bone engineering, bone regeneration or bone repair.

In some embodiments, this invention provides an osteoconductive and/or osteoinductive biomatrix, suitable for bone and dental application.

In some embodiments, this invention provides a hydrogel biomatrix or kit for use in applications for the treatment, amelioration, delay of pathogenesis, reduction of incidence or prevention of subchndral edema or bone marrow edema, foot and ankle fusions, spinal fusions, distal radius fusions, interbody lumbar spine fusion, fractures with metaphyseal comminution, tibial plateau fractures, Synthetic backfill after bone graft, distal radius fractures, calcaneal fractures, pilon fractures, proximal humorous fractures, tumours and cysts, lower extremity wounds or infection, anterior lumbar interbody spinal fusion, tibial fractures, cranio facial skeletal surgery, or others, as will be appreciated by the skilled artisan.

In some embodiments, this invention provides a hydrogel biomatrix or kit for use in applications making use of a gap filler, for example, in any bone fracture, such as in hands or feet, or any appropriate setting. In some embodiments, this invention provides a hydrogel biomatrix or kit for use in applications making use of a bone fastening device, such as a bone screw and for reinforcing the insertion and placement and maintenance of the same. In some embodiments, this invention provides a hydrogel biomatrix or kit for use in applications making use of a bone prosthetic device, and for reinforcing the insertion and placement and maintenance of the same.

In some embodiments, the term bone formation, or osteogenesis, refers to the creation of new bone mass or the repair of fractures, including non-union fractures. In some embodiments, the process comprises new bone structure growth or increased density of existing bone. In one embodiment, bone mass and/or fracture healing are assessed by histology, X-ray photographs, computerized X-ray densitometry, computerized fluorescence densitometry, or another method known in the art, or any combination thereof.

In one embodiment, the methods of this invention may be used to enhance bone formation in a subject, wherein said subject may be, in one embodiment, a vertebrate, and in another embodiment, the vertebrate is a mammal, including domestic animals, such as pigs, cattle, horses, sheep and goats and also including pets such as dogs, cats and experimental mammals, such as rodents. In another embodiment, the subject is a human. In some embodiments, the subject is male or female. In some embodiments, the subject has osteoporosis or bone frailty.

In some embodiments, the tissue whose engineering, regeneration or repair is desired is cartilage, thus this invention provides a method of inducing or enhancing cartilage formation in a subject comprising administering to said subject a biomatrix comprising a hydrogel conjugated to a aragonite or calcite, wherein said biomatrix is optionally seeded with a precursor cell, which can participate in said cartilage engineering, cartilage regeneration or cartilage repair, or in another embodiment administering to the subject a hydrogel comprising aragonite or calcite biomatrix, wherein said biomatrix is optionally seeded with a precursor cell, which can participate in said cartilage engineering, cartilage regeneration or cartilage repair.

In one embodiment, the phrase "cartilage repair" refers to restoring a cartilage defect to a more healthful state. In one embodiment, restoring cartilage results in regeneration of cartilage tissue. In one embodiment, restoring cartilage results in regeneration of a full thickness articular cartilage defect. In one embodiment, restoring cartilage results in complete regeneration of cartilage tissue at a site of cartilage repair. In one embodiment, cartilage repair may result in restoration/repair of missing or defective bone tissue, wherein repair of a cartilage defect necessitates removal of bone tissue at a site of cartilage repair. In one embodiment, cartilage repair comprises restoring cartilage defects of joints (e.g. knee, elbow, hip joints), of ears, of a nose, or of a wind pipe.

In one embodiment, the cartilage defect results from a trauma, a tear, a sports injury, a joint defect, or a repetitive stresses injury (e.g., osteochondral fracture, secondary damage due to cruciate ligament injury). In one embodiment, the cartilage disorder comprises a disease of the cartilage. In one embodiment, methods of this invention induce or enhance cartilage repair in osteoarthritis, rheumatoid arthritis, aseptic necrosis, osteochondritis dissecans, articular cartilage injuries, chondromalacia patella, chondrosarcoma, chondrosarcoma—head and neck, costochondritis, enchondroma, hallux rigidus, hip labral tear, osteochondritis dissecans, torn meniscus, relapsing polychondritis, canine arthritis, fourth branchial arch defect or cauliflower ear. In one embodiment, methods of this invention induce or enhance cartilage repair in degenerative cartilagenous disorders comprising disorders characterized, at least in part, by degeneration or metabolic derangement of connective tissues of the body, including not only the joints or related structures, including muscles, bursae (synovial membrane), tendons, and fibrous tissue, but also the growth plate, meniscal system, and intervertebral discs.

In one embodiment, the methods of the present invention are useful for the regeneration of tissue of various types, including bone, cartilage, tendon, ligament, muscle, skin, and other connective tissue, as well as nerve, cardiac, liver, lung, kidney, pancreas, brain, and other organ tissues.

The present invention encompasses use of biomatrices and/or kits as described herein for inducing or enhancing cartilage formation. In one embodiment, the biomatrix may be administered in solid form. In another embodiment, the biomatrix may be administered locally which in one embodiment is directly to a site of cartilage and/or bone infirmity or to a site of desired cartilage and/or bone formation. In one embodiment, the biomatrix may be machined into a variety of configurations, and quite complex shapes such as cylindrical structures and threaded structures may be formed by appropriate machine processing. In another embodiment, the biomatrix may be administered in solid blocks, rods or granular forms. In one embodiment, the biomatrices are shaped in such a way as to conform to the shape of existing cartilage and/or bone or to fill gap and contour defects in cartilage and/or bone. In one embodiment, the biomatrix is implanted in an orientation that allows it to contact the maximum surface area of an adjacent cartilage and/or bone.

The present invention encompasses use of biomatrices and/or kits as described herein for applications promoting dental health. In some embodiments, hydrogel biomatrices and kits comprising the same may find application in horizontal and vertical augmentation, sinus lifting, treating/preventing/ameliorating maxillofacial defects, treating/preventing/ameliorating cranial defects, treating/preventing/ameliorating alveolar ridge defects, treating/preventing/ameliorating periodontal defects and other related applications.

The present invention encompasses use of biomatrices and/or kits as described herein for applications promoting wound healing The present invention encompasses use of biomatrices and/or kits as described herein for applications in treating, ameliorating, reducing the incidence or severity of avascular necrosis, bone tumors, cysts and others.

The biomatrices can be applied to any appropriate site, as suiting the particular application. In some embodiments, non-limiting examples of sites to which the biomatrices of this invention may be applied include the spine, ribs, knee, pelvis, femur, tibia, ear, meniscus for a knee or elbow; vertebra, skull, disk, a joint; an articular surface of a bone, hip, nose, ligament, bronchial tube intervertebral disc, or structure in the oral cavity.

When such biomatrices are implanted at a site of cartilage and/or bone injury, cartilage and/or bone formation occurs. In one embodiment, such biomatrices lead to more rapid and increased quality cartilage and/or bone formation, lead to extensive remodeling, show evidence of integration and lead to new cartilage and/or bone with improved organization and strength.

In one embodiment, cartilage and/or bone formation in vivo and/or in vitro may be evaluated using one or more of the following markers. In one embodiment, since the functional hallmark of osteoblasts is their ability to mineralize the ECM, the incorporation of calcium into newly formed tissue (alizarin red staining) and the deposition of phosphate (von Kossa staining) as a measure of bone nodule formation may be followed. Possible fat accumulation, which would indicate differentiation of MSCs into adipocytes in the newly formed tissue, may also be monitored (oil red O staining). Differentiation of MSCs into osteoblasts may be evaluated in terms of alkaline phosphatase activity, an indicator of early osteoblast differentiation, and concentration of osteocalcin, which is secreted only by mature osteoblasts. Tissue formation may be evaluated in terms of concentrations of type I collagen, which is specific to bone, and DNA levels may be used as a measure of cell proliferation. Methods for cartilage detection are well known, for example via standard H & E, Safranin O, Masson trichrome or toluidine blue staining of histologic sections. Collagen type II staining by immunohistochemical methods may also serve as a marker In one embodiment, the subject receiving the composition of the present invention has osteoporosis. In another embodiment, the subject has Paget's disease, fibrous dysplasias, or osteodystrophies. In another embodiment, the subject has bone infirmity. In another embodiment, the subject has other bone remodeling disorders include osteomalacia, rickets, rheumatoid arthritis, achondroplasia, osteochodrytis, hyperparathyroidism, osteogenesis imperfecta, congenital hypophosphatasia, fribromatous lesions, multiple myeloma, abnormal bone turnover, osteolytic bone disease, periodontal disease, or a combination thereof. In one embodiment, bone remodeling disorders include metabolic bone diseases which are characterized by disturbances in the organic matrix, bone mineralization, bone remodeling, endocrine, nutritional and other factors which regulate skeletal and mineral homeostasis, or a combination thereof. Such disorders may be hereditary or acquired and in one embodiment, are systemic and affect the entire skeletal system.

Thus, in one aspect the human may have a bone remodeling disorder. Bone remodeling as used herein refers to the process whereby old bone is being removed and new bone is being formed by a continuous turnover of bone matrix and mineral that involves bone resorption by osteoclasts and bone formation by osteoblasts.

Osteoporosis is a common bone remodeling disorder characterized by a decrease in bone density of normally mineralized bone, resulting in thinning and increased porosity of bone cortices and trabeculae. The skeletal fragility caused by osteoporosis predisposes sufferers to bone pain and an increased incidence of fractures. Progressive bone loss in this condition may result in a loss of up to 50% of the initial skeletal mass.

Primary osteoporosis includes idiopathic osteoporosis which occurs in children or young adults with normal gonadal function, Type I osteoporosis, also described as post-menopausal osteoporosis, and Type II osteoporosis, senile osteoporosis, occurs mainly in those persons older than 70 years of age. Causes of secondary osteoporosis may be endocrine (e.g. glucocorticoid excess, hyperparathyroidism, hypoganodism), drug induced (e.g. corticosteroid, heparin, tobacco) and miscellaneous (e.g. chronic renal failure, hepatic disease and mal-absorption syndrome osteoporosis).

Those susceptible towards developing a bone deficit may be beneficiaries of the methods of the present invention. In one embodiment, subjects susceptible to osteoporosis include post-menopausal women, elderly males (e.g. those over the age of 65), males on hormone-deprivation therapy for prostate cancer treatment or another reason, and those being treated with drugs known to cause osteoporosis as a side-effect (e.g. steroid-induced osteoporosis). Certain factors are well known in the art which may be used to identify those at risk of developing a bone deficit due to bone remodeling disorders such as osteoporosis. Important factors include low bone mass, family history, life style, estrogen or androgen deficiency and negative calcium balance. Post-menopausal women are particularly at risk of developing osteoporosis.

The methods of the invention may also be used to enhance bone formation in conditions where a bone deficit is caused by factors other than bone remodeling disorders. Such bone deficits include fractures, bone trauma, conditions associated with post-traumatic bone surgery, post-prosthetic joint surgery, post plastic bone surgery, bone chemotherapy, post dental surgery and bone radiotherapy. Fractures include all types of microscopic and macroscopic fractures. In one embodiment, some examples of fractures includes avulsion fracture, comminuted fracture, transverse fracture, oblique fracture, spiral fracture, segmental fracture, displaced fracture, impacted fracture, greenstick fracture, torus fracture, fatigue fracture, intraarticular fracture (epiphyseal fracture), closed fracture (simple fracture), open fracture (compound fracture) and occult fracture. In one embodiment, fractures meant to be treated using the methods of the present invention are non-union fractures.

In one embodiment, this method may be used to: augment long bone fracture repair; generate bone in segmental defects; provide a bone graft substitute for fractures; facilitate tumor reconstruction or spine fusion; provide a local treatment (by injection) for weak or osteoporotic bone, such as in osteoporosis of the hip, vertebrae, or wrist, or a combination thereof. In another embodiment, the invention provides a method to accelerate the repair of fractured long bones; treat of delayed union or non-unions of long bone fractures or pseudoarthrosis of spine fusions; induce new bone formation in avascular necrosis of the hip or knee, or a combination thereof.

In one embodiment, the prosthetic or implant devices and other shaped products or structures of the present invention are provided for medical or related purposes. The term "medical or related purposes" is used throughout this specification to include the fields of human and non-human medicine and dentistry in particular. In one embodiment, a composition of the present invention may be used for restoration or replacement of both broken and diseased bone for orthopaedic, cranial, maxillofacial, dental and ocular and orbital floor implants. In another embodiment, a composition of the present invention may be used to replace lost bone trabeculae, which in one embodiment, may improve the mechanical strength of fixation for hip fractures.

In another embodiment, this invention provides a method of organ or tissue engineering in a subject, comprising the step of administering to a subject a composition comprising a biomatrix of this invention, seeded with a precursor cell in culture, optionally in the presence of a chelator. In another embodiment, this invention provides a method of organ or tissue repair or regeneration in a subject, comprising the step of administering to a subject a a biomatrix of this invention, seeded with a precursor cell in culture, optionally in the presence of a chelator.

In one embodiment, the methods of this invention are useful in engineering, repairing or regenerating a connector tissue. The term "connector tissue" refers, in one embodiment to a tissue physically attached to two different tissues, providing a physical connection between them. In one embodiment, the connector tissue fulfills a non-specific connection, such as, for example, the presence of fascia. In another embodiment, the connector tissue confers functional properties, such as for example, tendons, ligament, articular cartilage, and others, where, in one embodiment, proper functioning of one or both tissues thereby connected is dependent upon the integrity, functionality, or combination thereof of the connector tissue.

For example, and in one embodiment, tendon attachment to bone, involves the insertion of collagen fibers (Sharpey's fibers) into the bone. The fibers have a distinct architecture, as compared to that of the collagen in the tendon, and in the bone. The mineral structure differs as well, in that tendons are free of hydroxyapatite, however, at regions, which are in closer proximity to the bone, the collagen fibers are calcified, by an increased hydroxyapatite crystal incorporation, and at regions of apposition to bone becomes essentially indistinguishable, in terms of its composition.

In one embodiment, use of the biomatrices of this invention for repair, regeneration of tissue is in cases where native tissue is damaged, in one embodiment, by trauma. In one embodiment, the coral of this invention is useful in repairing, regenerating or engineering the connector tissue, and in another embodiment, in facilitating the establishment of physical connections to the tissues, which connector tissue connects. For example, tendon repair, as well as its reattachment to bone may be facilitated via the use of the gradient scaffolds of this invention, and represents an embodiment thereof. In another embodiment, the gradient scaffold allows for incorporation of individual cells, which are desired to be present in the developing/repairing/regenerating tissue.

In one embodiment, cell adhesion is a complex process that is important for maintaining tissue integrity and generating physical and permeability barriers within the body. Cell adhesion is mediated by specific cell surface adhesion molecules (CAMs). Among the many different families of CAMs, including the immununoglobulin, integrin, and selectin superfamilies, cadherins are a rapidly expanding family of calcium-dependent CAMs. The classical cadherins are integral membrane glycoproteins that generally promote cell adhesion through homophilic interactions (a cadherin on the surface of one cell binds to an identical cadherin on the surface of another cell), although cadherins also appear to be capable of forming heterotypic complexes with one another under certain circumstances and with lower affinity. Cadherins have been shown to regulate epithelial, endothelial, neural and cancer cell adhesion, with different cadherins expressed on different cell types. N (neural)-cadherin is predominantly expressed by neural cells, endothelial cells and a variety of cancer cell types. E (epithelial)-cadherin is predominantly expressed by epithelial cells. Other cadherins are P (placental)-cadherin, which is found in human skin and R (retinal)-cadherin.

This invention is further directed to use of cadherin-upregulating biomatrices for treating cancer or inhibiting cancer progression. Growth of mesenchymal stem cells on a biomatrix of this invention, in some embodiments upregulates cadherin mRNA.

Without being bound by theory, Applicants propose that, in one embodiment, contact of MSCs with the $CaCO_3$ biomatrix leads to high calcium concentration and calcium uptake that may in turn affect the stabilization of the extracellular domain of cadherin molecules and/or stimulate their expression through calcium signaling. β-catenin can be found in three cellular locations: bound to the cadherin molecules, in the cytoplasm, interacting with the APC, GSK and axin complex, or in the nucleus, acting as a coactivator for LEF/TCF. Normally, β-catenin is phosphorylated by GSK, ubiquitinized, and targeted for degradation. When Wnt ligand binds to its receptor; it activates Dsh, which in turn inactivates GSK. β-catenin accumulates in the cytoplasm, enters the nucleus and interacts with the transcription factors to activate the expression of target genes. Thus, stabilization and/or expression of cadherins can modulate β-catenin signaling.

In some aspects, it is unexpectedly found that hydogels allow for an advantage associated with the therapeutic effect seen with use of the same, over that of the use of a marine organism skeletal derivative biomatrix provided as a solid substrate alone, or solid substrates incorporating a coating comprising some of the therapeutic elements described herein, which are not found within a hydrogel.

In some aspects, it is unexpectedly found that hydogels allow for greater directed healing in sites of repair in use of the same, as opposed to use of a marine organism skeletal derivative biomatrix provided as a solid substrate alone, or in solid substrates incorporating a coating comprising some of the therapeutic elements described herein, which are not found within a hydrogel.

In some aspects, it is unexpectedly found that hydogels allow for less inflammation in sites of repair in use of the same, as opposed to use of a marine organism skeletal derivative biomatrix provided as a solid substrate alone, or in solid substrates incorporating a coating comprising some of the therapeutic elements described herein, which are not found within a hydrogel. It is found that the marine organism skeletal derivative particles facilitate the exposure of the elements within the particles the influence the healing. Furthermore, the release of substances, ions, biological factors are controlled through the hydrogel and have less burst effects compared to a solid substance alone. Furthermore, hydrogels may be manipulated, injected, press fitted into the site and conform to the wound or defect size and shape thereby reduce the voids between the biomatrix and tissue. Hydrogels may be altered to better fit patient specific and site/location specific density, strength, viscosity requirements. In other embodiments, specific release of factors incorporated within the hydrogel may be controlled, for example by altering the particle size distribution and hydrogel viscosity in the hydrogels of this inveiton. Furthermore, different compositions of hydrogels can be mixed for different patients, or implantation sites, to suit a particular application. Hydrogel scaffolds may be printed in a three dimension printer in order to fit the size, shape and porosity required. Therapeutic agents such as drugs, growth factors may be added and released in a controlled manner. In one embodiment, "treating" refers to both therapeutic treatment and prophylactic or preventative measures, wherein the object is to prevent or lessen the targeted pathologic condition or disorder as described hereinabove. Thus, in one embodiment, treating may include directly affecting or curing, suppressing, inhibiting, preventing, reducing the severity of, delaying the onset of, reducing symptoms associated with the disease, disorder or condition, or a combination thereof. Thus, in one embodiment, "treating" refers inter alia to delaying or inhibiting progression, expediting remission, inducing remission, augmenting remission, speeding recovery, increasing efficacy of or decreasing resistance to alternative therapeutics, or a combination thereof. In one embodiment, "preventing" refers, inter alia, to delaying the onset of symptoms, reducing the incidence of the disease, prolonging the remission of a disease, or treating a precursor of a disease, or a combination thereof. In another embodiment, preventing refers to preventing relapse to a disease, decreasing the number or frequency of relapse episodes, increasing latency between symptomatic episodes, or a combination thereof. In one embodiment, "suppressing" or "inhibiting", refers inter alia to reducing the severity of symptoms, reducing the severity of an acute episode, reducing the number of symptoms, reducing the incidence of disease-related symptoms, reducing the latency of symptoms, ameliorating symptoms, reducing secondary symptoms, reducing secondary infections, prolonging patient survival, or a combination thereof.

In one embodiment, symptoms are primary, while in another embodiment, symptoms are secondary. In one embodiment, "primary" refers to a symptom that is a direct result of a disease or disorder, while in one embodiment, "secondary" refers to a symptom that is derived from or consequent to a primary cause. In one embodiment, the compositions for use in the present invention treat primary or secondary symptoms or secondary complications.

In another embodiment, "symptoms" may be any manifestation of a disease or pathological condition, comprising inflammation, swelling, fever, pain, bleeding, itching, runny nose, coughing, headache, migraine, dizziness, blurry vision, etc., or a combination thereof. In one embodiment, symptoms comprise itchy eyes, swollen eyelids, redness, irritation, watery eyes, mucoid discharge, pain, or a combination thereof.

It is to be understood that for any of the methods as herein described the biomatrices administered may comprise any additional, or multiple additional agents of interest to achieve a desired result.

Sustained or directed release biomatrices can be formulated, e.g., to comprise liposomes or those wherein an agent of interest is protected with differentially degradable coatings, e.g., by microencapsulation, multiple coatings, etc. It is also possible to freeze-dry the agents and use the lyophilisates obtained. In one embodiment, the biomatrices of the present invention may be an extended release formulation for the agent of interest, or the suspended particle, or both, in some embodiments. In one embodiment, the expression "extended release", as used herein, includes, without limitation various forms of release, such as controlled release, timed release, sustained release, delayed release, long acting, and pulsatile delivery, immediate release that occurs with various rates. The ability to obtain extended release, controlled release, timed release, sustained release, delayed release, long acting, pulsatile delivery or immediate release is performed using well-known procedures and techniques available to the ordinarily skilled artisan.

In one embodiment of the invention, the concentrations of the biomatrices will depend on various factors, including the nature of the condition to be treated, the condition of the patient, the route of administration and the individual tolerability of the compositions.

It will be appreciated that the actual preferred amounts of active composition in a specific case will vary according to the particular compositions formulated, the mode of application, and the particular conditions and organism being treated. Dosages for a given host can be determined using conventional considerations, e.g., by customary comparison of the differential activities of the subject compounds and of a known agent, e.g., by means of an appropriate, conventional pharmacological protocol.

In one embodiment, the biomatrices of the invention may be administered acutely for acute treatment of temporary conditions, or may be administered chronically, especially in the case of progressive, recurrent, or degenerative disease. In one embodiment, one or more biomatrices of the invention may be administered simultaneously, or in another embodiment, they may be administered in a staggered fashion. In one embodiment, the staggered fashion may be dictated by the stage or phase of the disease.

Some embodiments of the invention are described by the non-limiting examples provided hereinbelow.

EXAMPLES

Example 1

Physical Properties Variability in Coralline-Based Solid Substrates of this Invention Materials and Methods A diamond disk saw was used to remove an outer coral layer, and large sections from which representative smaller sections of desired dimensions were cut from the coral block.

Coral from the hydrocoral *Porites lutea* which has an average pore size of 100-150 µm was harvested from various regions within a coral. The coral was evaluated visually for its appearance, density, and porosity. Coral was then optionally immersed in 5% sodium hypochlorite for removal of external organic tissue. Briefly, coral was first exposed to a 5% sodium hypochlorite solution for 30 minutes, 3 exchanges at temperature range RT at 50° C., and sub-atmospheric pressure using vacuum pressure ranging from 0.2-0.00001 Bar. The coral sections were then exposed to a 10% solution of hydrogen peroxide for 15 minutes at a temperature range of from RT-50° C., and subatmospheric pressure using vacuum pressure ranging from 0.2-0.00001 Bar. The cleaned sections were then washed in distilled water for 30 minutes, 3 exchanges at a temperature range of from RT-50° C., and sub-atmospheric pressure using vacuum pressure ranging from 0.3-0.00001 Bar.

The coral was optionally sterilized by exposure to gamma radiation at a strength of at least 22.5 kGy and can then be stored aseptically, in packaging material, and in particular, the smaller samples were irradiated, whereas larger blocks assessed were not irradiated.

Each section was then place in a plastic petri dish and 2 ml of fluid was applied to each dish. Observations regarding absorption of the fluid were recorded. Fluids used included animal blood, plasma, water and various colored solutions.

Results

To determine whether sample removal from various regions provides for materials, which vary in their physical characteristics and whether such variability provides for alternative qualities to the same, blood and other fluids listed were applied to the coral samples and absorption of the fluid within the coral samples was assessed.

FIG. 1 depicts the results of a representative absorption study conducted as described. Coral samples were isolated from different regions of a coral block, and assessed for their pattern and intensity of absorption of blood applied thereto. Surprisingly, there appears to be no uniformity in terms of the absorption profile, and the same is not an "all or none" phenomenon.

Figure 1B:
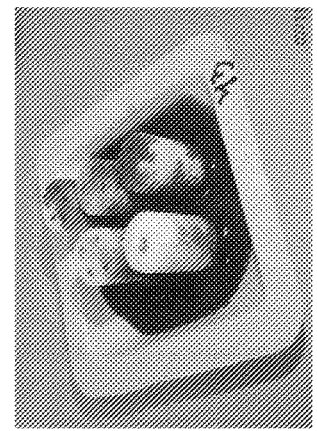
Figure 1A:
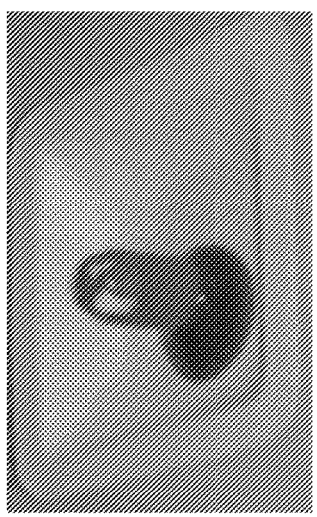
Figure 1F:
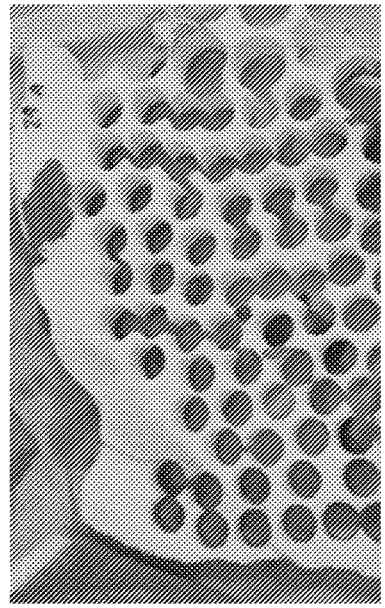
FIGS. 1D-1F show a larger block of the coral solid substrate from which the smaller implants were isolated.
Figure 1E:
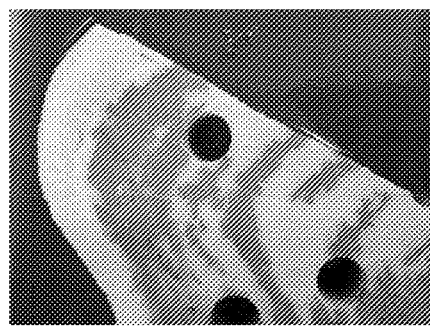
Figure 1D:
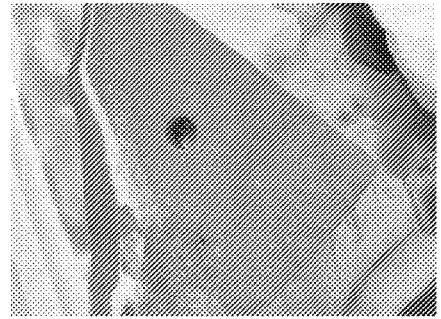

FIG. 1A for example, shows reasonably substantial absorption throughout the structure, whereas FIG. 1C shows poor to no absorption throughout, and FIG. 1B provides an interim phenomenon within the structure in that some regions substantially absorb the fluid and some regions absorb minimal to no fluid. FIGS. 1D-1F show cross-sectional slices through coral pieces from which coral plugs were cut and prepared, providing different patterns of absorption within the macrostructures, as well.

Other fluids were assessed in terms of their absorption within parallel samples comparable to the sample in FIG. 1C. To serve as a stain, a salt solution, and protein solution, carbohydrate solutions, ionic solutions were prepared and applied, and the results substantially mirrored that of the applied blood in that poor to no absorption occurred in the sample of FIG. 1C. Plain water applied thereto provided substantially the same, resulting in poor to no absorption within the coral sample of FIG. 1C.

FIGS. 1D-1F provide images of larger blocks of coral from which the samples of FIGS. 1A-1C were taken, respectively. As can be seen in FIG. 1D, the region from which the sample of 1A was taken shows good uptake of the fluid applied, in this case, blood, whereas the region from which the sample was taken in FIG. 1C (i.e. the block of FIG. 1F) shows minimal uptake, and the region from which the sample of Figure 1B was taken, shown in FIG. 1E shows an intermediate uptake, in that some regions show good uptake, whereas other regions show minimal uptake.

As demonstrated herein, the size of the sample assessed is not limiting, and indeed samples of various sizes and thicknesses may be thus assessed. Furthermore, differences in surface tension are evident (compare FIG. 1C to FIG. 1A).

Example 2

Establishing a Screening Protocol for Coralline-Based Solid Substrates

Figure 2:
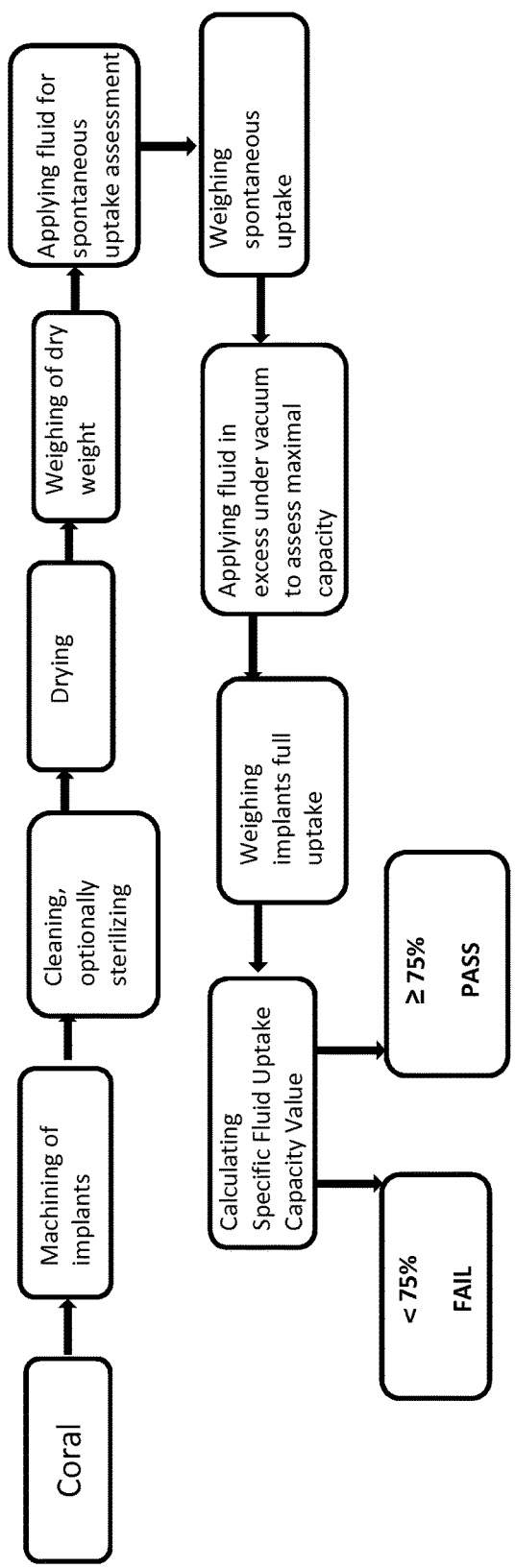
FIG. 2 presents a flow chart for an embodied screening protocol for the identification of optimized marine organism skeletal derivative-based solid substrates for promoting cell or tissue growth or restored function.

Based on the findings in Example 1, a screening protocol may be established to select for an optimized coral-based solid substrate for promoting cell or tissue growth or restored function. FIG. 2 provides a flow diagram of an envisioned screening protocol process. Coral samples are identified, isolated and machined to a desired size and shape, or assessed in blocks. The samples are then cleaned and optionally sterilized, then dried. The coral sample being assessed may be dried under vacuum and/or heated toward this end.

A dry weight for each sample may then be recorded.

Fluid as described herein is added to each assay container in an approximately 1:1 ratio or slightly more, i.e. equal to or slightly more than the size of the sample in mm as compared to the volume of fluid in ml is added to the container.

The sample may then be weighed and a spontaneous fluid uptake value is determined.

Samples may optionally be dried, prior to further manipulation of the sample.

A significantly increased amount of fluid is brought into contact with the sample and a vacuum is applied for a period of time to ensure maximal uptake of the applied fluid into the coral sample.

A total fluid uptake capacity is assessed and the specific fluid uptake capacity value is determined by dividing the spontaneous fluid uptake value by the total fluid uptake capacity.

If the value exceeds the cutoff value of 75%, then the sample will be noted for its suitability as a solid substrate for promoting cell or tissue growth or restored function. When the sample is utilized in vivo in subsequent applications, in some aspects, the sample is first contacted with autologous biological fluids or materials from the host prior to implantation into the same. If the value is less than the stated cutoff value, then the sample is not used as a solid substrate for promoting cell or tissue growth or restored function.

Example 3

Improved Solid Substrate Incorporation as a Function of Certain Physical Properties in Coralline-Based Solid Substrates of this Invention In order to assess the consequence of the phenotypic variability in blood absorption in the plugs of Example 1, coral plugs were prepared using a standard production method including three hypochlorite washes, hydrogen peroxide treatment and multiple double distilled water washes. Their spontaneous fluid uptake and total fluid uptake values were determined as described in Example 2, with water being the sample fluid assessed in this case. Sample implants exhibiting a spontaneous fluid uptake value of more than 75% were also checked for their spontaneous blood uptake ability.

Implants were graded as red, white, and intermediate, with intermediate referring to regions that are red and regions that remain white. Implants were placed in each goat knee so that each goat received an implant characterized by a spontaneous fluid uptake value of more than 75% and second implant was inserted, which implant was characterized by a spontaneous fluid uptake value of less than 50%. The animals were followed for 4 weeks and then sacrificed.

Figure 3B:
FIGS. 3A-3D demonstrate the correlation between biologic fluid uptake before implantation and site healing over time of a 10 by 12 mm implant in the medial femoral chondyle in a goat. Implantation sites treated with implants characterized by significant water and blood uptake, or minimal uptake thereof within the implant before implantation, were evaluated macroscopically, at 4 weeks post. Tissue consistent with hyaline cartilage appearance substantially covered the implant, in samples with significant fluid uptake, whereas samples which were characterized by minimal/diminished fluid uptake presented with a more fibrous capsule covering over the implant implantation (FIG. 3A versus 3C, respectively). X-ray analysis of the respective implants characterized by minimal/diminished fluid uptake (FIG. 3B) versus those characterized by significant fluid uptake (FIG. 3D) demonstrated that implants characterized by significant fluid uptake appeared to be properly integrated within the implantation site with no significant adverse reaction, while implants characterized by minimal/diminished fluid uptake appeared to have radiolucent lines surrounding the implant and induce bone resorption and loss of mechanical integrity.
Figure 3D:
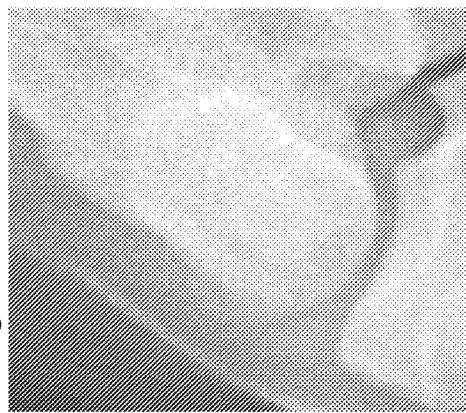
Figure 3A:
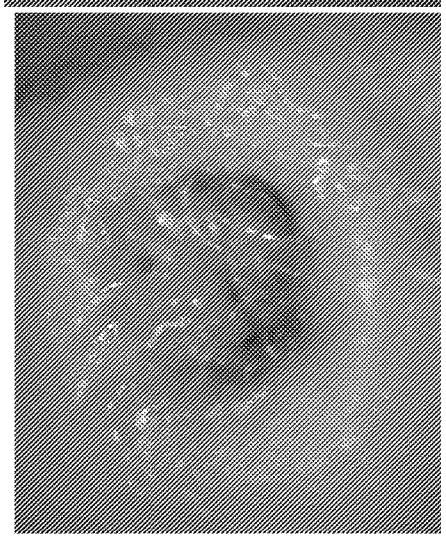
Figure 3C:
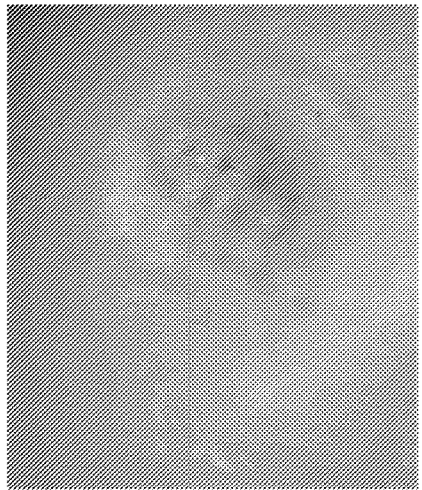

Early cartilage formation was assessed macroscopically and histologically. Osteointegration and early bone formation or resorption was assessed using X-ray, micro-CT and histology FIGS. 3A-3D demonstrate the correlation between biologic fluid uptake before implantation and site healing over time of a 10 by 12 mm implant in the medial femoral chondyle in a goat. Implantation sites treated with implants characterized by significant water and blood uptake, or minimal uptake thereof within the implant before implantation, were evaluated macroscopically, at 4 weeks post. Tissue consistent with hyaline cartilage appearance substantially covered the implant, in samples with significant fluid uptake, whereas samples which were characterized by minimal/diminished fluid uptake presented with a more fibrous capsule covering over the implant implantation (FIG. 3A versus 3C, respectively). X-ray analysis of the respective implants characterized by minimal/diminished fluid uptake (FIG. 3B) versus those characterized by significant fluid uptake (FIG. 3D) demonstrated that implant characterized by significant fluid uptake appeared to be properly integrated within the implantation site with no significant adverse reaction, while implants characterized by minimal/diminished fluid uptake appeared to have radiolucent lines surrounding the implant and induce bone resorption and loss of mechanical integrity.

Example 4

Prescreening Coralline-Based Solid Substrates for Implantation

For applications in promoting cell or tissue growth or restored function, solid substrates are assessed for their ability to absorb fluid, such as, for example, water. Substrates that provide a specific fluid uptake capacity value of at least 75% are then implanted in the desired tissue site. For example, and representing one embodiment, such a solid substrate may be implanted within cartilage and neighboring bone for applications in repairing or regeneration in osteochondral defects or disease.

Solid substrates may be prepared according to any embodiment as described herein, as will be appreciated by the skilled artisan.

The substrates are envisioned for use in veterinary applications, as well as in the treatment of human subjects. At appropriate intervals, standard methodology is employed to assess good incorporation of the substrates and healing of the affected tissue, for example, X-ray, CT or MRI imaging may be performed to verify the position of the implants.

Implantation may be at any suitable location, for example, for knee joint repair, implantation may be within the Medial Femoral Condyle (MFC), Lateral Femoral Condyle (LFC), Patela, Trochlear Groove (TG) and the Tibia.

In applications relating to promoting cell or tissue growth or restored function, it is noted that solid substrates characterized by a specific fluid uptake capacity value of at least 75% will significantly outperform solid substrates characterized by a specific fluid uptake capacity value of less than 40%, in terms of their ability to promote cell or tissue growth or restored function at the site, promote healing at the implantation site, promote returned tissue function, or a combination thereof.

Example 5

Physical Properties Variability in Coralline-Based Solid Substrates of this Invention Natural surfaces are heterogenic due to their variable material composition, surface roughness and porosity and thus demonstrate variable water repellence/adhesion characteristics. Contact angle measurements can characterize the wetting of rough surfaces, taking into account the topography and the chemical structure of the surface.

Contact angle measurement was with goiniometry. The contact angle is an equilibrium contact angle measured macroscopically on a solid surface. The same is to be distinguished from Young contact angles, measured on atomically smooth, chemically homogeneous surfaces.

The regions were classified into three classes and their relative surface areas were approximated as a percentage out of the total surface area:

Regions characterized by contact angles of between 0 and 60 deg, appear as white regions in the figures provided. Regions characterized by a contact angle of between 60 and 90 deg and regions characterized by a contact angle of 90 deg and higher also appear in the figures provided.

Water drops of 1 ul-10 ul volume were deposited on cleaned and dried coral samples with a precise micro-dosing syringe. The contact angles were measured with a Rame-Hart goniometer (Model 500) with an accuracy of 0.1 deg (Bormashenko, 2012). Measurements were assessed for both sides of the drop and averaged. The test medium employed was normal saline (0.9%).

Three 3×3 mm coral samples termed, R43, R34, R44 were assessed. Prior to evaluation of contact angles, the specific fluid uptake capacity value was assessed for samples from each block, and the results are presented in Table 2.

| Coral | Specimen (Name) | specific fluid uptake capacity value |
|---|---|---|
| 43 | 1 | 0.62 |
|  | 2 | 0.46 |

-continued

| Coral | Specimen (Name) | specific fluid uptake capacity value |
|---|---|---|
|  | 3 | 0.60 |
|  | 4 | 0.31 |
|  | por1 | 0.17 |
|  | por2 | 0.17 |
|  | por3 | 0.37 |
| 44 | 1 | 0.32 |
|  | 2 | 0.82 |
|  | 3 | 0.88 |
| 34 | 1 | 0.70 |
|  | 2 | 0.39 |
|  | 3 | 0.33 |

Figure 4B:
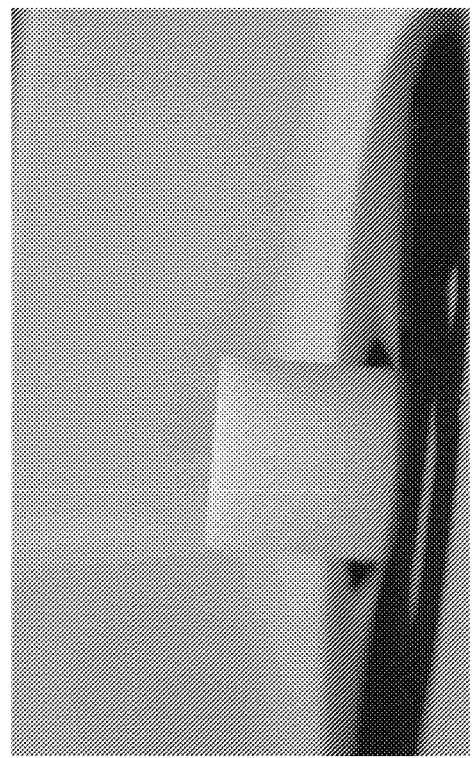
FIG. 4A-4B provides photographs of coral sample specimens evaluated for their contact angles.
Figure 4A:
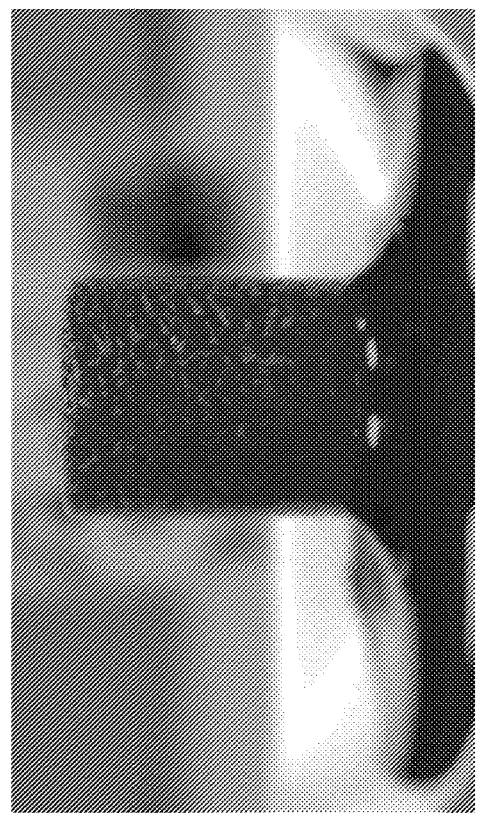

FIGS. 4A-4B provide photographs of coral sample specimens evaluated for their contact angles. FIG. 4A shows plugs cut from a larger block, which were assessed for their contact angle characterization. Samples assessed as that of FIG. 4A provided for a contact angle primarily of a smaller degree as herein described. Samples as that in FIG. 4B provided for a larger contact angle as herein described.

Figure 5C:
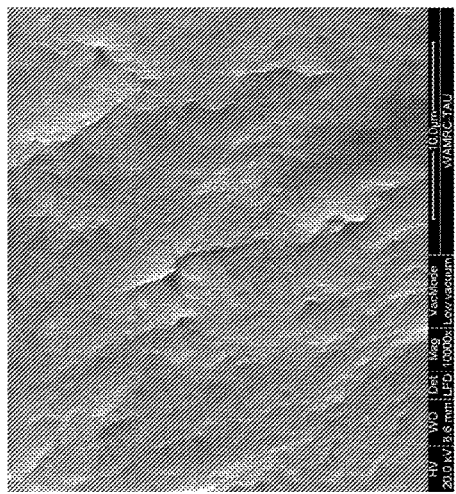
FIG. 5 demonstrates the microscopic structure as determined by ESEM, of isolated substrates characterized by minimal biologic fluid uptake, versus those characterized by substantial biologic fluid uptake at various magnifications in samples with minimal biologic fluid uptake indicate a much smoother external surface as compared to samples with substantial uptake where the aragonite crystals are readily seen (FIGS. 5A-5C versus 5D-5F).
Figure 5B:
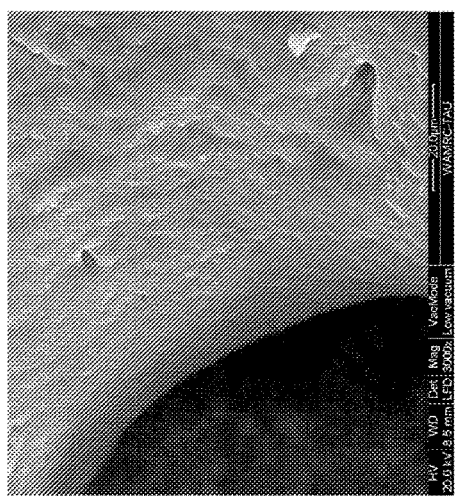
Figure 5A:
Figure 5F:
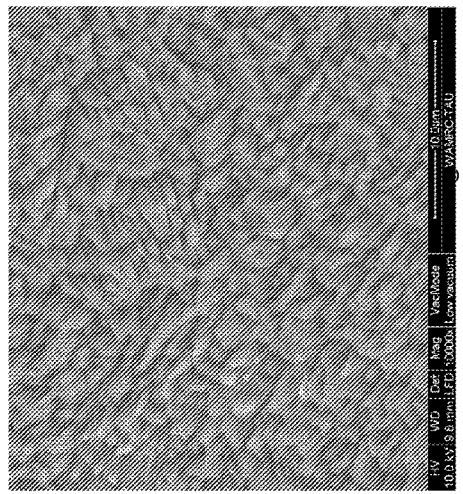
Figure 5E:
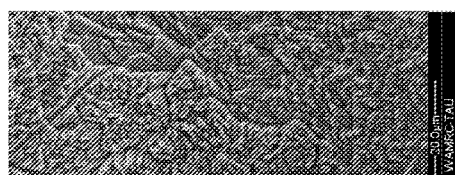
Figure 5D:
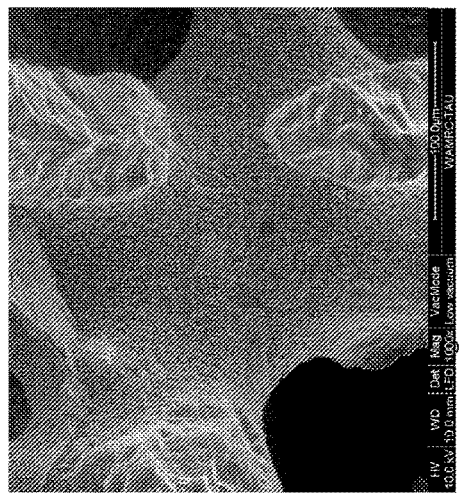

FIGS. 5A-5C provide photographs of coral sample R34 specimens evaluated for their contact angles. FIG. 5A shows regions cut from the larger block, which were assessed for their contact angle characterization. The majority of regions of the block assessed in FIGS. 5B and 5C provided for a contact angle primarily of less than 60 degrees. Certain areas in FIGS. 5B and 5C provided for a contact angle of between 60 and 90 degrees and over 90 degrees (shaded regions). FIG. 6 FIGS. 6A and 6B similarly provide photographs of coral sample R44 specimens evaluated for their contact angles. FIG. 6A shows regions cut from the larger block, which were assessed for their contact angle characterization. The majority of regions of the block assessed in FIG. 6B provided for a contact angle primarily of less than 60 degrees. Certain areas in FIG. 6B provided for a contact angle of between 60 and 90 degrees and over 90 degrees (shaded regions).

The contact angle measurements parallel the specific fluid uptake capacity values obtained for respective coral samples. Accordingly, the improved solid substrates for promoting cell or tissue growth or restored function of this function may be characterized by either a determination of a contact angle, or a specific fluid uptake capacity value.

Furthermore, environmental scanning electron microscopy (ESEM) studies confirmed the results of the contact angle studies presented herein.

Table 3 presents the specific fluid uptake capacity values for the coral samples evaluated by ESEM.

| Coral | Specimen (Name) | specific fluid uptake capacity value |
|---|---|---|
| R27 | 7 | 0.87 |
| R30 | 40 | 0.04 |
| R43 | 1 | 0.62 |

The results of ESEM analysis conducted on the samples described in Table 3 showed that in samples assessed from the R27-7 block provided for a zero drop angle value, and no drop formation was seen. Sample R30-40 was taken following application of fluid, and it was noted that the sample failed to "wet" when water was applied. Following desiccation, water droplets were evident on the surface, consistent with a phenotype of poor surface wetting.

The results for sample R43-1 were consistent with those seen for sample R30-40.

Taken together, these results are corroborative of the contact angle data, as well specific fluid uptake capacity values obtained for respective coral samples. A sample having a specific fluid uptake capacity values obtained for respective coral samples of more than 75% exhibited no drop formation on the surface, consistent with a "good wetting" phenotype, whereas samples with a lower specific fluid uptake capacity value exhibited droplet formation during desiccation.

Example 6

Physical Properties Variability in Coralline-Based Solid Substrates of this Invention A porites coral was cut into plate pieces using an industrial saw machine, then the plate pieces' size was reduced using a jaw crusher machine. The material was milled using Pulverisette 6 (Fritsch GmbH, Germany) to obtain a median particle diameter of 4 mm. Finally, the particles were sieved using mesh in the following sizes:

Coral granules sizes:
0.2-0.7 mm
0.5-1.5 mm
1.5-2.5 mm
2-5 mm

Hydrogel Biomatrices, representing embodied biomatrices of this invention were then prepared making use of the ground coral particles, according to the following formulations:

| Particle size | Distribution A (Weight Percentage) | Distribution B (weight percentage) | Distribution C (weight percentage) |
|---|---|---|---|
| 0.2-0.7 | 20% | 100% | 0 |
| 0.5-1.5 | 20% | 0 | 0 |
| 1.5-2.5 | 30% | 0 | 0 |
| 2-5 | 30% | 0 | 100% |

Thinner biomatrices encompassing the hydrogels of this invention comprised the following materials, in various combinations:
Sodium carboxymethyl cellulose, Mw=250,000.cat no.419281-100G-Aldrich
Gelatin cat no.48723-500G-F,Fluka
PEG, MW 1,500. cat no.202436-250G-Aldrich
Alginic acid sodium, Medium MW, salt cat no.A2033-100G, Sigma Aldrich
Jonexa hylasten SGL-80, Genzyme (1%; 0.8% cross linked hayloronate)
Lifecore sodium HyaluronateMW2M, 3%
Dried sodium Hyaluronate MW=2M, 2%, Lifecore
Collagen type ICat. Nos. C1809, C7661, C9791, C8919, Sigma
Fibrin from human plasma, F5386-1G, Sigma
Fibrinogen from human plasma, F3879-1G,Sigma
Thrombin from human plasma, T6884-100UNSigma
Chitosan, Chitoceuticals®GMP compliant, with degree of 85-90% deacetylation MW of
10K-50K, HEPPE medical chitosan GmBH Thicker biomatrices encompassing the hydrogels of this invention comprised the following materials, in various combinations:
Calcium chloride anhydrous, cat no.C1016-100G—Sigma Aldrich
Calcium phosphatedibasic, cat no.C7263-500g—Sigma Aldrich
Calcium phosphate monobasic monohydrate, cat no.21053-500g—sigma Aldrich
Calcium phosphate, cat no.21218-1KG—Sigma Aldrich The hydrogels were then prepared as follows:
Coral granules were mixed with one or more of the following carriers:
Sodium alginate, Gelatin, Hyaluronic acid cross linked, Hyaluronic acid, Carboxymethyl Cellulose (CMC), PEG, Chitosan, Collagen typeI and Fibrinogen/thrombin.
Different carrier concentrations and coral granules to gelatin ratios were prepared.

Figure 7C:
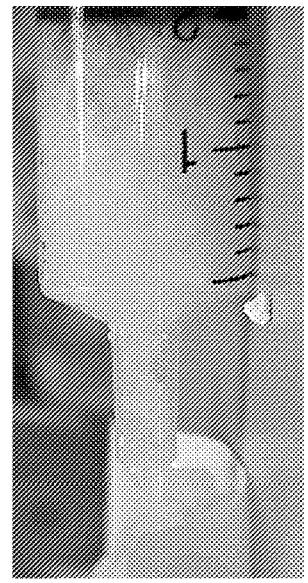
FIG. 7C shows a syringe.
Figure 7B:
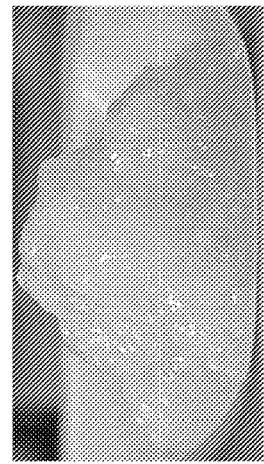
FIGS. 7A-7B depict hydrogel matrices comprised of gelatin 4% and coral granules mixtures in two particle size distributions A and B, respectively.
Figure 7A:

Formulation 1 was prepared as follows: Gelatin at 2% and 4% were prepared (1 g or 2 g in 50 ml DDW) by heating to 60° C. with agitation for 30 min. Then a mixture of coral granules with gelatin was prepared at a ratio of 1:1. The mixture was left to cool down and settle at room temperature for at least 30 min. Two particle size distributions were prepared, distribution A, and distribution B. The mixture was transferred to a syringe and is shown in FIGS. 7A (distribution A) and 7B (distribution B). The mixture was viscous and easy to handle.

Figure 8B:
FIGS. 8A-8B depict hydrogel matrices comprised of Sodium Alginate 2% and coral granules, before and after cross linking with $CaCl_2$, respectively.
Figure 8A:
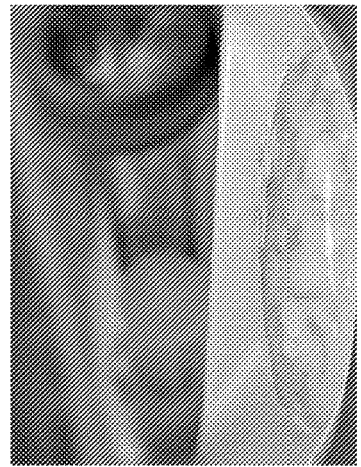

Formulation 2 was prepared as follows: Sodium Alginate with medium MW, at 2% (1 g in 50 ml saline) was dissolved overnight with stirring and agitation. For complete dissolution the solution was heated to 60° C. and stirred for 1 h. Then a mixture of coral granules using distribution C with sodium alginate was prepared at a ratio of 1:1 and cross linked with 100 mM $CaCl_2$ for 10 min. The obtained gel is solid but soft and flexible as can be seen in FIG. 8, showing photographs of the hydrogel obtained prior to (FIG. 8A) and following (FIG. 8B) cross linking.

Figure 9A:
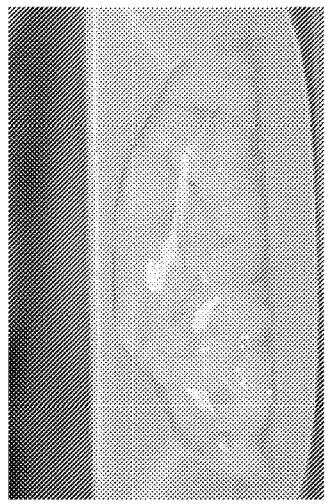
FIGS. 9A-9B depict hydrogel matrices comprised of CMC 2% with and without ~1 mm coral granules in a syringe, respectively.
Figure 9B:
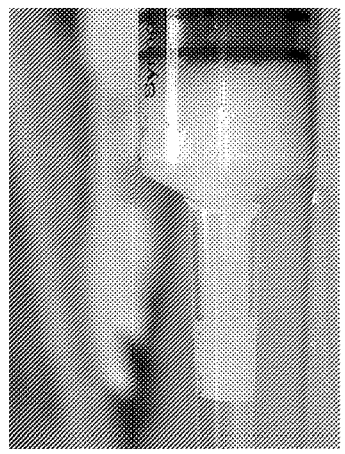

Formulation 3 was prepared as follows: Carboxymethyl Cellulose (CMC) at 2% and 4% (1 g or 2 g in 50 ml DDW) was dissolved over night with agitation. Then a mixture of coral granules with Carboxymethyl Cellulose was prepared at a ratio of 1:1 using distribution B. The resulting mixture, shown in FIG. 9B, was viscous and easy to handle, as compared to FIG. 9A (which shows CMC alone).

Figure 10A:
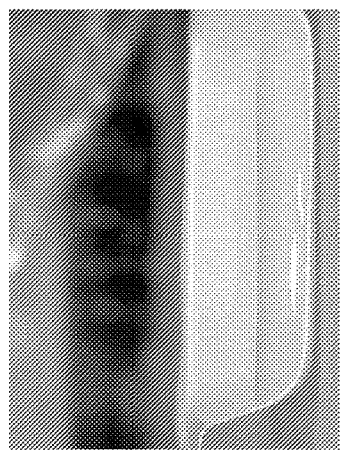
FIGS. 10A-10B depict hydrogel matrices comprised of mixtures of coral granules with Hyaluronantes from two different commercial sources.
Figure 10B:
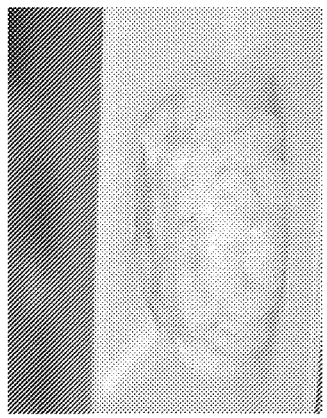

Formulation 4 was prepared as follows: Two types of hyaluronic acids were used: Jonexa hylasten SGL-80, Genzyme (1% total and 0.8% cross linked hyaloronate) and Lifecore sodium Hyaluronate 2M, 3%. Mixtures of coral granules using distribution C with Hyaluronic acid were prepared at a ratio of ~1:1. Each resulting mixture, i.e. Lifecore sodium Hyaluronate (shown in FIG. 10A) and Genzyme sodium Hyaluronate (shown in FIG. 10B), was viscous and easy to handle.

Figure 11:
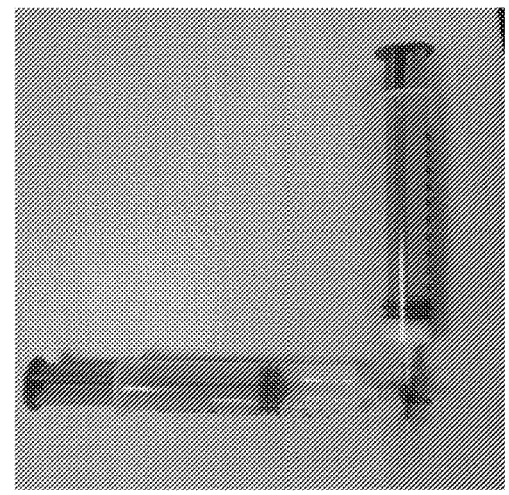
FIG. 11 depicts an embodied two syringe gel formation for the matrices of this invention.

Formulation 5 was prepared as follows: A collagen 0.1% solution was prepared in 0.1M acetic acid, and allowed to stir at room temperature for 3 hours. Fibrinogen at 2% was dissolved slowly in PBS at 37 degrees for 4 hours. The solution was swirled gently every 30 minutes. Coral granules using distribution A were mixed with Collagen and Fibrinogen at a ratio of 1:1:1 (w/w) and inserted into one syringe and thrombin was added with a second syringe to a final concentration of 10 U/ml. (FIG. 11). The mixture was incubated for 10 minutes at room temperature. The Coral-Collagen-fibrin gel formed and was kept at 4° C.

Combinations with covalently cross linked collagen gel will also be prepared by using cross linking agents such as glutaraldehyde, EDC NHS and or by using DHT method (dehydrothermally (DHT) cross-linked by heating at 80° C. for 48 h under a vacuum of 0.067 mBar).

Formulation 6 was prepared as follows: Hyaluronic acid at 2% and 4% (1 g or 2 g in 50 ml DDW) each was dissolved over night with mild agitation. A collagen 0.1% solution was prepared in 0.1M acetic acid, and allowed to stir at room temperature for 3 hours. Fibrinogen at 2% was dissolved slowly in PBS at 37 degrees for 4 hours. The solution was swirled gently every 30 minutes. Coral granules using distribution A were mixed with Hyaluronic acid, Collagen, Fibrinogen at a ratio of 1:1:1:1 (w/w) and thrombin was added to a final concentration of 10 U/ml. The mixture was incubated for 10 minutes at room temperature. The coral-HA-collagen-fibrin gel formed and kept at 4° C. Combinations with covalently cross linked collagen gel will also be prepared by using cross linking agents such as glutaraldehyde, Ribose, EDC NHS and or by using DHT method.

Formulation 7 was prepared as follows: Hyaluronic acid at 2% and 4% (1 g or 2 g in 50 ml DDW) was dissolved over night with mild agitation. Chitosan at 2%-6% was prepared in saline or in DDW for 30 min at room temperature. Coral granules were mixed with Hyaluronic acid and chitosan at a ratio of 1:1:1. The coral-HA-Chitosan gel was formed and kept at 4° C.

Combinations with covalently cross linked HA-chitosan gel will also be prepared by using cross linking agents such as EDC NHS and or glutaraldehyde.

Figure 12B:
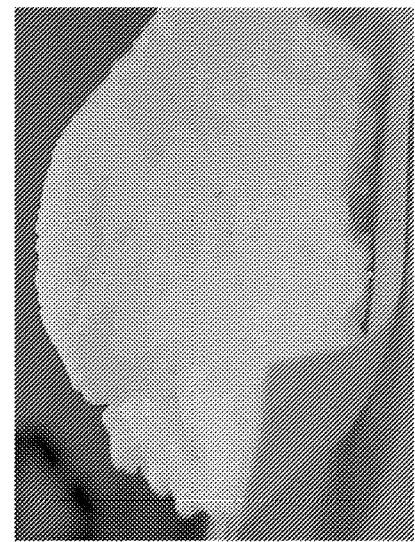
FIGS. 12A-12B depict coral granules with Brushite cement.
Figure 12A:
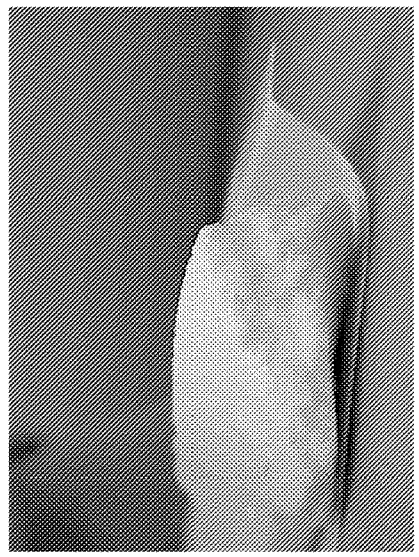

Formulation 8 was prepared as follows: Brushite cement, also known as Dicalcium phosphate Dihydrate (DCPD) ($CaHPO_4.2H_2O$), is obtained by mixing β-Tricalcium phosphate (beta-TCP) and Monocalcium phosphate monohydrate (MCPM) ($Ca(H_2PO_4)2H_2O$) and water. A powder mixture was prepared by mixing of 1 g β-tricalcium phosphate, 0.5 g monocalcium phosphate monohydrate, and 0.5 g Coral granules using distribution A. 2 ml DDW were added and setting took place for several minutes. The end result is brushite that acts as a binder forming bridges between the beta-TCP particles while engulfing the coral granules (FIGS. 12A-12B).

Other matrices such as cements can be used as a composite bone graft composed of coral granules and cement matrix.

Bone void fillers are an envisioned embodied application of the materials of this invention. Such fillers will be comprised of, inter alia, coral based materials (powders, particles, granules, beads etc), mixed with one or more hydrogel materials and or viscous hydrophilic polymers as described above.

Mixtures with hydrogel carriers such as PEG (poly ethylene glycol) and or PEG-DA (diacrylate), Chitosan, Collagen type1, sodium Alginate, Fibrinogen/thrombin, fibrin, PVA (poly vinyl alcohol), PLGA or poly(lactic-co-glycolic acid), poly(epsilon-caprolactone) (PCL), poly(L-lactide) (PLA), Agarose, Pluronic (temperature dependent hydrogels), will be used in bone fillers formulations.

Coral based materials can be mixed with hydrogels and or bone cement materials such as amorphous calcium phosphate (ACP), dicalcium phosphate dihydrate (DCPD), dicalcium phosphate anhydrous (DCPA), β-tricalcium phosphate (β-TCP), dicalcium phosphate (DCP), tetracalcium phosphate (TTCP), monocalcium phosphate monohydrate (MCPM) and calcium carbonate (CC).

Hydrogels materials in different concentrations, percentage (% w/v), molecular weights, different cross linkers will produce various hydrogels with different characterizations such as dissolution and absorption time, strength and tissue adhesion capacity It will be understood by those skilled in the art that various changes in form and details may be made therein without departing from the spirit and scope of the invention as set forth in the appended claims. Those skilled in the art will recognize, or be able to ascertain using no more than routine experimentation, many equivalents to the specific embodiments of the invention described herein. Such equivalents are intended to be encompassed in the scope of the claims.

In one embodiment of this invention, "about" refers to a quality wherein the means to satisfy a specific need is met, e.g., the size may be largely but not wholly that which is specified but it meets the specific need of cartilage repair at a site of cartilage repair. In one embodiment, "about" refers to being closely or approximate to, but not exactly. A small margin of error is present. This margin of error would not exceed plus or minus the same integer value. For instance, about 0.1 micrometers would mean no lower than 0 but no higher than 0.2. In some embodiments, the term "about" with regard to a reference value encompasses a deviation from the amount by no more than 5%, no more than 10% or no more than 20% either above or below the indicated value.

In the claims articles such as "a", "an" and "the" mean one or more than one unless indicated to the contrary or otherwise evident from the context. Claims or descriptions that include "or" or "and/or" between members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention provides, in various embodiments, all variations, combinations, and permutations in which one or more limitations, elements, clauses, descriptive terms, etc., from one or more of the listed claims is introduced into another claim dependent on the same base claim unless otherwise indicated or unless it would be evident to one of ordinary skill in the art that a contradiction or inconsistency would arise. Where elements are presented as lists, e.g. in Markush group format or the like, it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in haec verba herein. Certain claims are presented in dependent form for the sake of convenience, but Applicant reserves the right to rewrite any dependent claim in independent format to include the elements or limitations of the independent claim and any other claim(s) on which such claim depends, and such rewritten claim is to be considered equivalent in all respects to the dependent claim in whatever form it is in (either amended or unamended) prior to being rewritten in independent format.

What is claimed is:

1. A hydrogel biomatrix cement comprising
(a) a hydrogel that comprises a biocompatible polymer and a coral or coral derivative biomatrix,
the biomatrix being in the form of a powder, granule, bead, emulsion, suspension, paste or putty, wherein the coral or coral derivative biomatrix in the powder, granule, bead, emulsion, suspension, paste or putty was prepared from coral characterized as having a specific fluid uptake capacity value of at least 75%, which specific fluid uptake capacity value is a percentage determined by establishing a spontaneous fluid uptake value divided by a total fluid uptake value using water, and wherein the biocompatible polymer is not a natural polymer, the hydrogel being mixed with (b) β-tricalcium phosphate, monocalcium phosphate monohydrate, dicalcium phosphate, tetra-calcium phosphate, calcium sulfate or hydroxyapatite, wherein the spontaneous fluid uptake is the difference in weight of the biomatrix before and after contacting dried biomatrix with the fluid for 0.1-1 minute, and the total fluid uptake is the difference in weight of the biomatrix before and after contacting biomatrix with fluid under vacuum for a period of time sufficient to ensure maximal uptake of the fluid into the matrix.

2. The hydrogel biomatrix cement of claim 1, wherein said coral or coral derivative from which the biomatrix in the powder, granule, bead, emulsion, suspension, paste or putty was prepared is characterized by also having a contact angle value of less than 70 degrees, when in contact with a fluid.

3. The hydrogel biomatrix cement of claim 1, wherein said derivative is a coral.

4. The hydrogel biomatrix cement of claim 3, wherein said coral or coral derivative is aragonite, calcite, hydroxyapatite, mixtures thereof, or other polymorphs of the same.

5. The hydrogel biomatrix cement of claim 1, wherein said powder, granules, beads, emulsion, suspension, paste or putty comprises aragonite or calcite particles.

6. The hydrogel biomatrix cement of claim 5, wherein said aragonite or calcite particles are about 1-20 microns in diameter.

7. The hydrogel biomatrix cement of claim 5, wherein said aragonite or calcite particles are about 20-400 microns in diameter.

8. The hydrogel biomatrix cement of claim 5, wherein said aragonite or calcite particles are about 50-800 nanometers in diameter.

9. The hydrogel biomatrix cement of claim 1, wherein said biomatrix comprises aragonite or calcite conjugated to said hydrogel.

10. The hydrogel biomatrix cement of claim 9, wherein said hydrogel comprises platelet rich plasma, a glycosaminoglycan or a combination thereof.

11. The hydrogel biomatrix cement of claim 1, wherein said cement further comprises a cytokine, a growth factor, a chelator, a cell population, a therapeutic compound, a drug, or any combination thereof.

12. The hydrogel biomatrix cement of claim 11, wherein said biomatrix comprises said therapeutic compound or drug, and said therapeutic compound or drug comprises an anti-inflammatory compound, an anti-infective compound, a pro-angiogenic factor or a combination thereof.

13. The hydrogel biomatrix cement of claim 1, wherein said hydrogel further comprises a chondrogenic support agent, an osteogenic support agent or a combination thereof.

14. The hydrogel biomatrix cement of claim 1, wherein the hydrogel is in gel form.

15. The hydrogel biomatrix cement of claim 1, wherein the biomatrix is in the form of an emulsion, suspension, paste or putty.

16. A kit for tissue engineering, tissue regeneration or tissue repair comprising the hydrogel biomatrix cement of claim 1.

17. A method of tissue engineering, tissue regeneration or tissue repair in a subject comprising administering to said subject the hydrogel biomatrix cement of claim 1.

18. The method of claim 17, wherein said biomatrix cement is seeded with a precursor cell that can participate in said tissue engineering, tissue regeneration or tissue repair.

19. The method of claim 17, wherein said tissue engineering, tissue regeneration or tissue repair results in the induction or enhancement of bone formation, cartilage formation or a combination thereof.

20. The method of claim 19, wherein said subject has osteoporosis.

21. The method of claim 19, wherein said subject has Paget's disease, fibrous dysplasia or osteodystrophy.

22. The method of claim 19, wherein said subject has bone infirmity.

23. The method of claim 19, wherein said hydrogel is administered to a site of bone infirmity.

24. The method of claim 19, wherein said enhancing bone formation comprises healing non-union fractures.

25. The method of claim 19, wherein said method treats a cartilage defect or disorder in said subject.

26. The method of claim 25, wherein said cartilage defect or disorder comprises a full thickness articular cartilage defect; osteoarthritis, a joint defect or a defect resulting from trauma, sports, or repetitive stress.

27. The method of claim 19, wherein said tissue engineering, tissue regeneration or tissue repair results in the induction or enhancement of cartilage formation.

28. The method of claim 27, wherein said method further comprises exposing said site of cartilage repair, and optionally exposing bone tissue located proximally to the site of cartilage repair in said subject and implanting said hydrogel biomatrix cement therein.

29. The method of claim 28, further comprising the step of affixing at least a portion of said hydrogel biomatrix cement to bone located proximally to said site of cartilage repair.

30. The method of claim 28, wherein said method promotes adhesion, proliferation or differentiation, or a combination thereof, of a cell population at said site of cartilage repair.

31. The method of claim 28, further comprising seeding said biomatrix with mesenchymal stem cells prior to said implanting.

32. The method of claim 28, wherein said method comprises positioning said hydrogel biomatrix cement below the upper limit of said site such that said hydrogel biomatrix cement does not protrude above an upper limit of said site.

33. The method of claim 19, wherein said subject is afflicted with a cartilage and/or bone defect or disorder or disease.

34. The method of claim 19, wherein said cartilage defect or disorder comprises a full or partial thickness articular cartilage defect; osteochondral defect; osteoarthritis, bone marrow edema, a joint defect or a defect resulting from trauma, sports, repetitive stress or osteoarthritis.

35. The method of claim 17, wherein said hydrogel biomatrix cement can be used as a bone filler or bone substitute material.

36. The method of claim 17, wherein said hydrogel biomatrix cement further comprises a bone filler or bone substitute material.

37. The method of claim 17, wherein said coral derivative comprises hydroxyapatite.

38. The method of claim 17, wherein said method further comprises forming a three-dimensional bone filler in sequential cross-sectional layers in accordance with a model of the bone filler, comprising said hydrogel biomatrix cement.

* * * * *